(12) United States Patent
Ivosev et al.

(10) Patent No.: US 10,651,019 B2
(45) Date of Patent: May 12, 2020

(54) SYSTEMS AND METHODS FOR IDENTIFYING PRECURSOR AND PRODUCT ION PAIRS IN SCANNING SWATH DATA

(71) Applicant: DH TECHNOLOGIES DEVELOPMENT PTE. LTD., Singapore (SG)

(72) Inventors: Gordana Ivosev, Etobicoke (CA); Nic G. Bloomfield, Newmarket (CA); Michael Murphy, Stouffville (CA); Stephen A. Tate, Barrie (CA)

(73) Assignee: DH Technologies Development Pte. Ltd., Singapore (SG)

(*) Notice: Subject to any disclaimer, the term of this patent is extended or adjusted under 35 U.S.C. 154(b) by 0 days.

(21) Appl. No.: 16/320,111

(22) PCT Filed: Jul. 19, 2017

(86) PCT No.: PCT/IB2017/054383
§ 371 (c)(1),
(2) Date: Jan. 24, 2019

(87) PCT Pub. No.: WO2018/020363
PCT Pub. Date: Feb. 1, 2018

(65) Prior Publication Data
US 2019/0228957 A1    Jul. 25, 2019

Related U.S. Application Data

(60) Provisional application No. 62/366,526, filed on Jul. 25, 2016.

(51) Int. Cl.
*H01J 49/00* (2006.01)
*G06F 17/16* (2006.01)

(52) U.S. Cl.
CPC .......... *H01J 49/0036* (2013.01); *G06F 17/16* (2013.01); *H01J 49/004* (2013.01);
(Continued)

(58) Field of Classification Search
CPC .. H01J 49/0036; H01J 49/004; H01J 49/0027; H01J 49/0081; H01J 49/0045; G06F 17/16
(Continued)

(56) References Cited

U.S. PATENT DOCUMENTS 9,472,387 B2 * 10/2016 Bloomfield ......... H01J 49/0027
10,128,093 B2 * 11/2018 Tate ................... H01J 49/0027
(Continued)

FOREIGN PATENT DOCUMENTS

WO    2014195785 A1    12/2014
WO    2015056065 A1    4/2015
WO    2015056066 A1    4/2015

OTHER PUBLICATIONS

International Search Report and Written Opinion for PCT/IB2017/054383, dated Nov. 9, 2017.

*Primary Examiner* — Michael Maskell
(74) *Attorney, Agent, or Firm* — John R. Kasha; Kelly L. Kasha; Kasha Law LLC

(57) ABSTRACT

A system is disclosed for identifying a precursor ion of a product ion in a scanning DIA experiment. A precursor ion mass selection window is scanned across a precursor ion mass range of interest, producing a series of overlapping windows across the precursor ion mass range. Each overlapping window is fragmented and mass analyzed, producing a plurality of product ion spectra for the mass range. A product ion is selected from the spectra. Intensities for the selected product ion are retrieved for at least one scan across the mass range producing a trace of intensities versus (Continued)

precursor ion m/z. A matrix multiplication equation is created that describes how one or more precursor ions correspond to the trace for the selected product ion. The matrix multiplication equation is solved for one or more precursor ions corresponding to the selected product ion using a numerical method.

15 Claims, 15 Drawing Sheets

(52) U.S. Cl.
CPC ...... *H01J 49/0027* (2013.01); *H01J 49/0045* (2013.01); *H01J 49/0081* (2013.01)

(58) Field of Classification Search
USPC .......................................... 250/281, 282, 288
See application file for complete search history.

(56) References Cited

U.S. PATENT DOCUMENTS

| | | |
|---|---|---|
| 2003/0168588 A1 | 9/2003 | Brailove et al. |
| 2009/0194688 A1 | 8/2009 | Bateman et al. |

\* cited by examiner

SYSTEMS AND METHODS FOR IDENTIFYING PRECURSOR AND PRODUCT ION PAIRS IN SCANNING SWATH DATA

CROSS REFERENCE TO RELATED APPLICATION

This application claims the benefit of U.S. Provisional Patent Application Ser. No. 62/366,526, filed Jul. 25, 2016, the content of which is incorporated by reference herein in its entirety.

INTRODUCTION

The teachings herein relate to the identification of precursor and product ion pairs in scanning SWATH data. More particularly the teachings herein relate to systems and methods for identifying one or more precursor ions responsible for a producing a product ion in scanning SWATH data utilizing the additional information provided by the scanning precursor ion mass selection window.

BACKGROUND

Scanning SWATH is a tandem mass spectrometry method. In general, tandem mass spectrometry, or MS/MS, is a well-known technique for analyzing compounds. Tandem mass spectrometry involves ionization of one or more compounds from a sample, selection of one or more precursor ions of the one or more compounds, fragmentation of the one or more precursor ions into product ions, and mass analysis of the product ions.

Tandem mass spectrometry can provide both qualitative and quantitative information. The product ion spectrum can be used to identify a molecule of interest. The intensity of one or more product ions can be used to quantitate the amount of the compound present in a sample.

A large number of different types of experimental methods or workflows can be performed using a tandem mass spectrometer. Three broad categories of these workflows are, targeted acquisition, information dependent acquisition (IDA) or data-dependent acquisition (DDA), and data-independent acquisition (DIA).

In a targeted acquisition method, one or more transitions of a precursor ion to a product ion are predefined for a compound of interest. As a sample is being introduced into the tandem mass spectrometer, the one or more transitions are interrogated during each time period or cycle of a plurality of time periods or cycles. In other words, the mass spectrometer selects and fragments the precursor ion of each transition and performs a targeted mass analysis for the product ion of the transition. As a result, a mass spectrum is produced for each transition. Targeted acquisition methods include, but are not limited to, multiple reaction monitoring (MRM) and selected reaction monitoring (SRM).

In an IDA method, a user can specify criteria for performing targeted or untargeted mass analysis of product ions while a sample is being introduced into the tandem mass spectrometer. For example, in an IDA method a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS is repeatedly performed on the precursor ions of the subset of precursor ions as the sample is being introduced into the tandem mass spectrometer.

In proteomics and many other sample types, however, the complexity and dynamic range of compounds is very large. This poses challenges for traditional targeted and IDA methods, requiring very high speed MS/MS acquisition to deeply interrogate the sample in order to both identify and quantify a broad range of analytes.

As a result, DIA methods, the third broad category of tandem mass spectrometry, were developed. These DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor or product ion scan. Instead a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

The precursor ion mass selection window used to scan the mass range can be very narrow so that the likelihood of multiple precursors within the window is small. This type of DIA method is called, for example, MS/MS$^{ALL}$. In an MS/MS$^{ALL}$ method, a precursor ion mass selection window of about 1 amu is scanned or stepped across an entire mass range. A product ion spectrum is produced for each 1 amu precursor mass window. A product ion spectrum for the entire precursor ion mass range is produced by combining the product ion spectra for each mass selection window. The time it takes to analyze or scan the entire mass range once is referred to as one scan cycle. Scanning a narrow precursor ion mass selection window across a wide precursor ion mass range during each cycle, however, is not practical for some instruments and experiments.

As a result, a larger precursor ion mass selection window, or selection window with a greater width, is stepped across the entire precursor mass range. This type of DIA method is called, for example, SWATH acquisition. In a SWATH acquisition, the precursor ion mass selection window stepped across the precursor mass range in each cycle may have a width of 5-25 amu, or even larger. Like the MS/MS$^{ALL}$ method, all the precursor ions in each precursor ion mass selection window are fragmented, and all of the product ions of all of the precursor ions in each mass selection window are mass analyzed. However, because a wider precursor ion mass selection window is used, the cycle time can be significantly reduced in comparison to the cycle time of the MS/MS$^{ALL}$ method. Or, for liquid chromatography (LC), the accumulation time can be increased. Generally for LC, the cycle time is defined by an LC peak. Enough points (intensities as a function of cycle time) must be obtained across an LC peak to determine its shape. When the cycle time is defined by the LC, the number of experiments or mass spectrometry scans that can be performed in a cycle defines how long each experiment or scan can accumulate ion observations. As a result, wider precursor ion mass selection window can increase the accumulation time.

U.S. Pat. No. 8,809,770 describes how SWATH acquisition can be used to provide quantitative and qualitative information about the precursor ions of compounds of interest. In particular, the product ions found from fragmenting a precursor ion mass selection window are compared to a database of known product ions of compounds of interest. In addition, ion traces or extracted ion chromatograms (XICs) of the product ions found from fragmenting a precursor ion mass selection window are analyzed to provide quantitative and qualitative information.

However, identifying compounds of interest in a sample analyzed using SWATH acquisition, for example, can be difficult. It can be difficult because either there is no precursor ion information provided with a precursor ion mass selection window to help determine the precursor ion that produces each product ion, or the precursor ion information provided is from a mass spectrometry (MS) observation that has a low sensitivity. In addition, because there is little or no specific precursor ion information provided with a precursor ion mass selection window, it is also difficult to determine if a product ion is convolved with or includes contributions from multiple precursor ions within the precursor ion mass selection window.

As a result, a method of scanning the precursor ion mass selection windows in SWATH acquisition, called scanning SWATH, was developed. Essentially, in scanning SWATH, a precursor ion mass selection window is scanned across a mass range so that successive windows have large areas of overlap and small areas of non-overlap. This scanning makes the resulting product ions a function of the scanned precursor ion mass selection windows. This additional information, in turn, can be used to identify the one or more precursor ions responsible for each product ion.

Scanning SWATH has been described in International Publication No. WO 2013/171459 A2 (hereinafter "the '459 application"). In the '459 application, a precursor ion mass selection window or precursor ion mass selection window of 25 Da is scanned with time such that the range of the precursor ion mass selection window changes with time. The timing at which product ions are detected is then correlated to the timing of the precursor ion mass selection window in which their precursor ions were transmitted.

The correlation is done by first plotting the mass-to-charge ratio (m/z) of each product ion detected as a function of the precursor ion m/z values transmitted by the quadrupole mass filter. Since the precursor ion mass selection window is scanned over time, the precursor ion m/z values transmitted by the quadrupole mass filter can also be thought of as times. The start and end times at which a particular product ion is detected are correlated to the start and end times at which its precursor is transmitted from the quadrupole. As a result, the start and end times of the product ion signals are used to determine the start and end times of their corresponding precursor ions.

Scanning SWATH has also been described in International Publication No. WO 2015/056066 A1 (hereinafter "the '066 application"). The '066 application improves the accuracy of the correlation of product ions to their corresponding precursor ions by combining product ion spectra from successive groups of the overlapping rectangular precursor ion mass selection windows. Product ion spectra from successive groups are combined by successively summing the intensities of the product ions in the product ion spectra. This summing produces a function that can have a shape that is non-constant with precursor mass. The shape describes product ion intensity as a function of precursor mass. A precursor ion is identified from the function calculated for a product ion.

The '459 application and the '066 application provide methods for identifying one or more precursor ions corresponding to a product ion in scanning SWATH data. However, additional systems and methods are needed to identify one or more precursor ions corresponding to a product ion in scanning SWATH data.

SUMMARY

A system is disclosed for identifying a precursor ion of a product ion in a scanning DIA tandem mass spectrometry experiment. The system includes an ion source device, mass filter, a fragmentation device, a mass analyzer, and a processor. The ion source device transforms a sample into an ion beam. The mass filter receives the ion beam and filters the ions by scanning a precursor ion mass selection window across a precursor ion mass range of interest. A series of overlapping precursor ion mass selection windows across the precursor ion mass range are produced.

The fragmentation device receives the precursor ions of each overlapping precursor ion mass selection window. The fragmentation device fragments the precursor ions of each overlapping precursor ion mass selection window.

The mass analyzer that receives the product ions from each fragmentation of each overlapping precursor ion mass selection window. The mass analyzer analyzes the resulting product ions. A product ion spectrum for each overlapping precursor ion mass selection window is produced, and a plurality of product ion spectra for the precursor ion mass range is produced.

The processor receives the plurality of product ion spectra produced by the series of overlapping precursor ion mass selection windows. The processor selects at least one product ion from the plurality of product ion spectra that has an intensity above a predetermined threshold. For the selected product ion, the processor retrieves the intensities of the selected product ion from the plurality of product ion spectra for at least one scan of the precursor ion mass selection window across the precursor ion mass range. A trace that describes how the intensity of the selected product ion varies with precursor ion mass-to-charge ratio (m/z) as the precursor ion mass selection window is scanned across the precursor ion mass range is produced.

The processor creates a matrix multiplication equation that describes how one or more precursor ions correspond to the trace for the selected product ion. The matrix multiplication equation includes a known n×m mass filter matrix multiplied by an unknown precursor ion column matrix of length m that equates to a selected ion trace column matrix of length n. The processor solves the matrix multiplication equation for the unknown precursor ion column matrix using a numerical method. Intensities for one or more precursor ion m/z values corresponding to the selected product ion are produced.

A method is disclosed for identifying a precursor ion of a product ion in a scanning DIA tandem mass spectrometry experiment. A sample is ionized and transformed into an ion beam using an ion source device. The ion beam is filtered by scanning a precursor ion mass selection window across a precursor ion mass range of interest using a mass filter. A series of overlapping precursor ion mass selection windows are produced across the precursor ion mass range.

The precursor ions of each overlapping precursor ion mass selection window are fragmented using a fragmentation device. The resulting product ions are analyzed using a mass analyzer. A product ion spectrum is produced for each overlapping precursor ion mass selection window resulting in a plurality of product ion spectra for the precursor ion mass range.

At least one product ion is selected from the plurality of product ion spectra that has an intensity above a predetermined threshold using a processor. For the selected product ion, the intensities of the selected product ion are retrieved from the plurality of product ion spectra for at least one scan of the precursor ion mass selection window across the precursor ion mass range using the processor. A trace is produced that describes how the intensity of the selected product ion varies with precursor ion m/z as the precursor ion mass selection window is scanned across the precursor ion mass range. A matrix multiplication equation is created that describes how one or more precursor ions corresponds to the trace for the selected product ion using the processor. The matrix multiplication equation includes a known n×m mass filter matrix multiplied by an unknown precursor ion column matrix of length m that equates to a selected ion trace column matrix of length n.

The matrix multiplication equation is solved for the unknown precursor ion column matrix using a numerical method using the processor. Intensities for one or more precursor ion m/z values are produced corresponding to the selected product ion.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
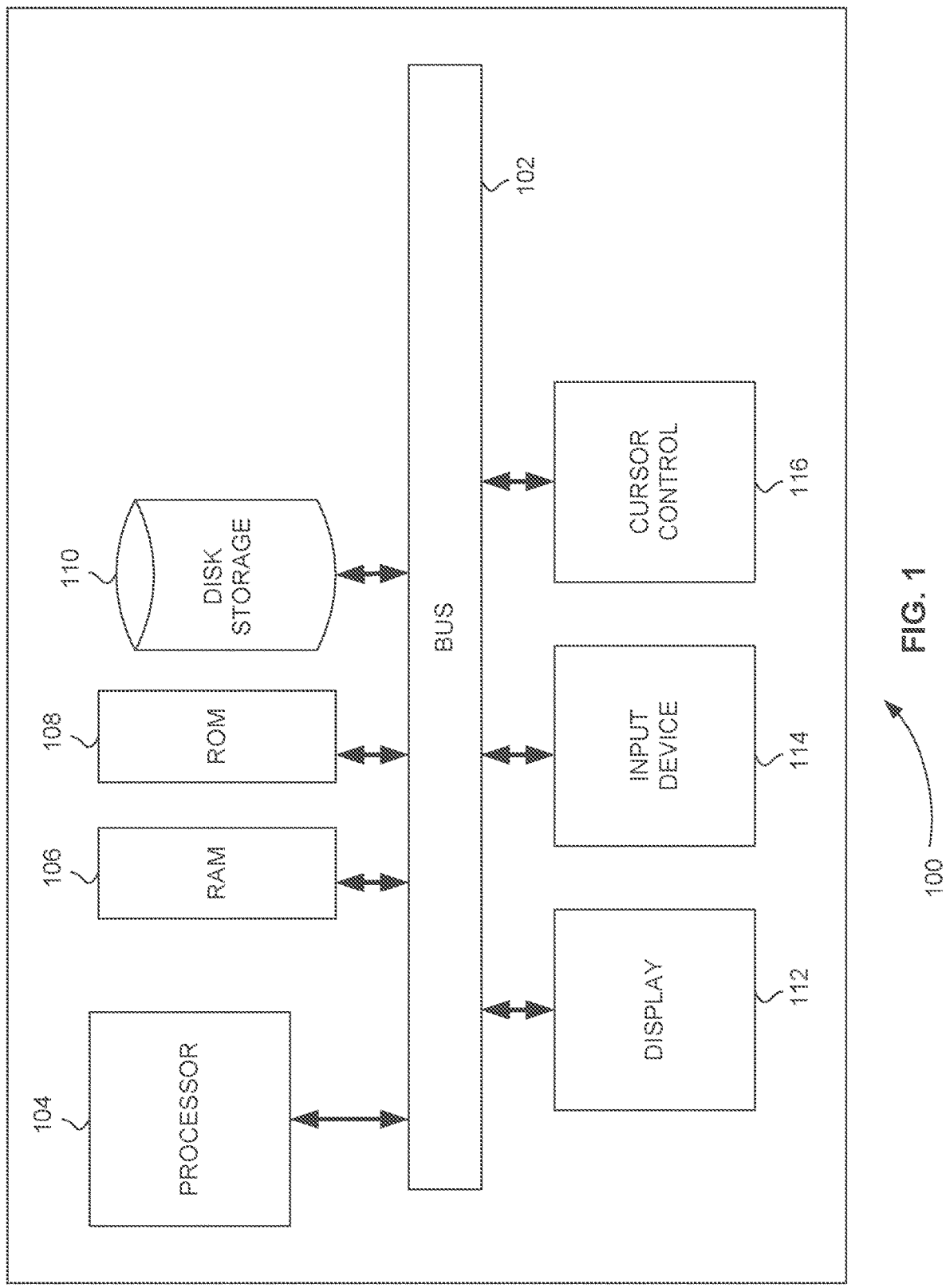
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and precursor ion mass selection media. Non-volatile media includes, for example, optical or magnetic disks, such as storage device 110. Volatile media includes dynamic memory, such as memory 106. Precursor ion mass selection media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Identifying Precursor Ions

As described above, identifying compounds of interest in a sample analyzed using SWATH acquisition, for example, can be difficult, because there is no precursor ion information provided with a precursor ion mass selection window to help determine the precursor ion that produces each product ion. As a result, a method of scanning the precursor ion mass selection windows in SWATH acquisition, called scanning SWATH, was developed. Essentially, in scanning SWATH, a precursor ion mass selection window is scanned across a mass range so that successive windows have large areas of overlap and small areas of non-overlap. This scanning makes the resulting product ions a function of the scanned precursor ion mass selection windows. This additional information, in turn, can be used to identify the one or more precursor ions responsible for each product ion.

The '459 application and the '066 application, which are described above, provide methods for taking advantage of this additional information to identify one or more precursor ions corresponding to a product ion in scanning SWATH data. However, additional systems and methods are needed to use this information and more accurately identify one or more precursor ions corresponding to a product ion in scanning SWATH data.

As described above, sequential windowed acquisition (SWATH) is a tandem mass spectrometry technique that allows a mass range to be scanned within a time interval using multiple precursor ion scans of adjacent or overlapping precursor ion mass selection windows. A mass filter selects each precursor mass window for fragmentation. A high-resolution mass analyzer is then used to detect the product ions produced from the fragmentation of each precursor mass window. SWATH allows the sensitivity of precursor ion scans to be increased without the traditional loss in specificity.

Unfortunately, however, the increased sensitivity that is gained through the use of sequential precursor mass windows in the SWATH method is not without cost. Each of these precursor mass windows can contain many other precursor ions, which confounds the identification of the correct precursor ion for a set of product ions. Essentially, the exact precursor ion for any given product ion can only be localized to a precursor mass window.

Figure 2:
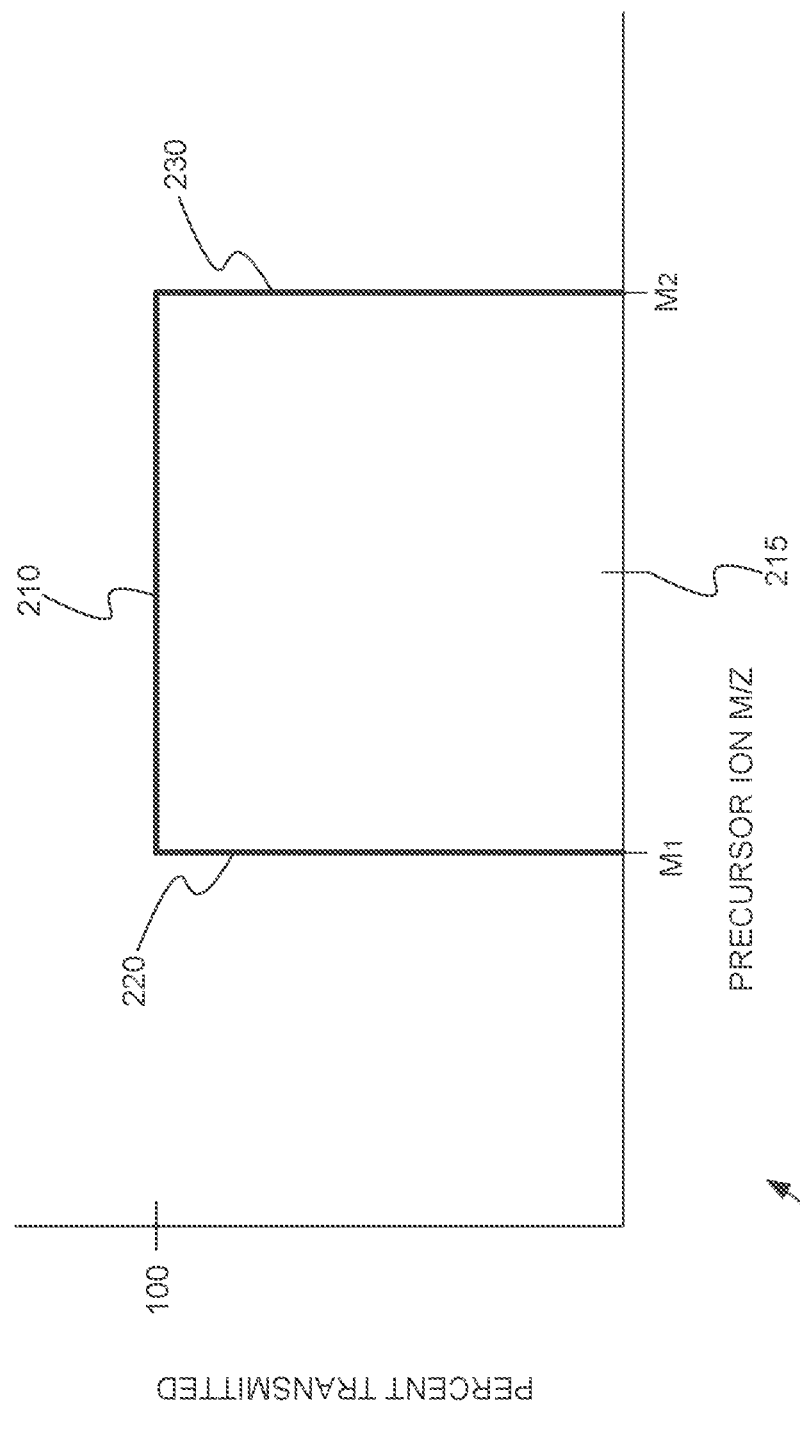
FIG. 2 is an exemplary plot of a single precursor ion mass selection window that is typically used in a SWATH acquisition, in accordance with various embodiments.

FIG. 2 is an exemplary plot 200 of a single precursor ion mass selection window that is typically used in a SWATH acquisition, in accordance with various embodiments. Precursor ion mass selection window 210 transmits precursor ions with m/z values between $M_1$ and $M_2$, has set mass or center mass 215, and has sharp vertical edges 220 and 230. The SWATH precursor ion mass selection window width is $M_2-M_1$. The rate at which precursor ion mass selection window 210 transmits precursor ions is constant with respect to precursor m/z. Note that one skilled in the art can appreciate that the terms "m/z" and "mass" can be used interchangeably. The mass is easily obtained from the m/z value by multiplying the m/z value by the charge.

Figure 3:
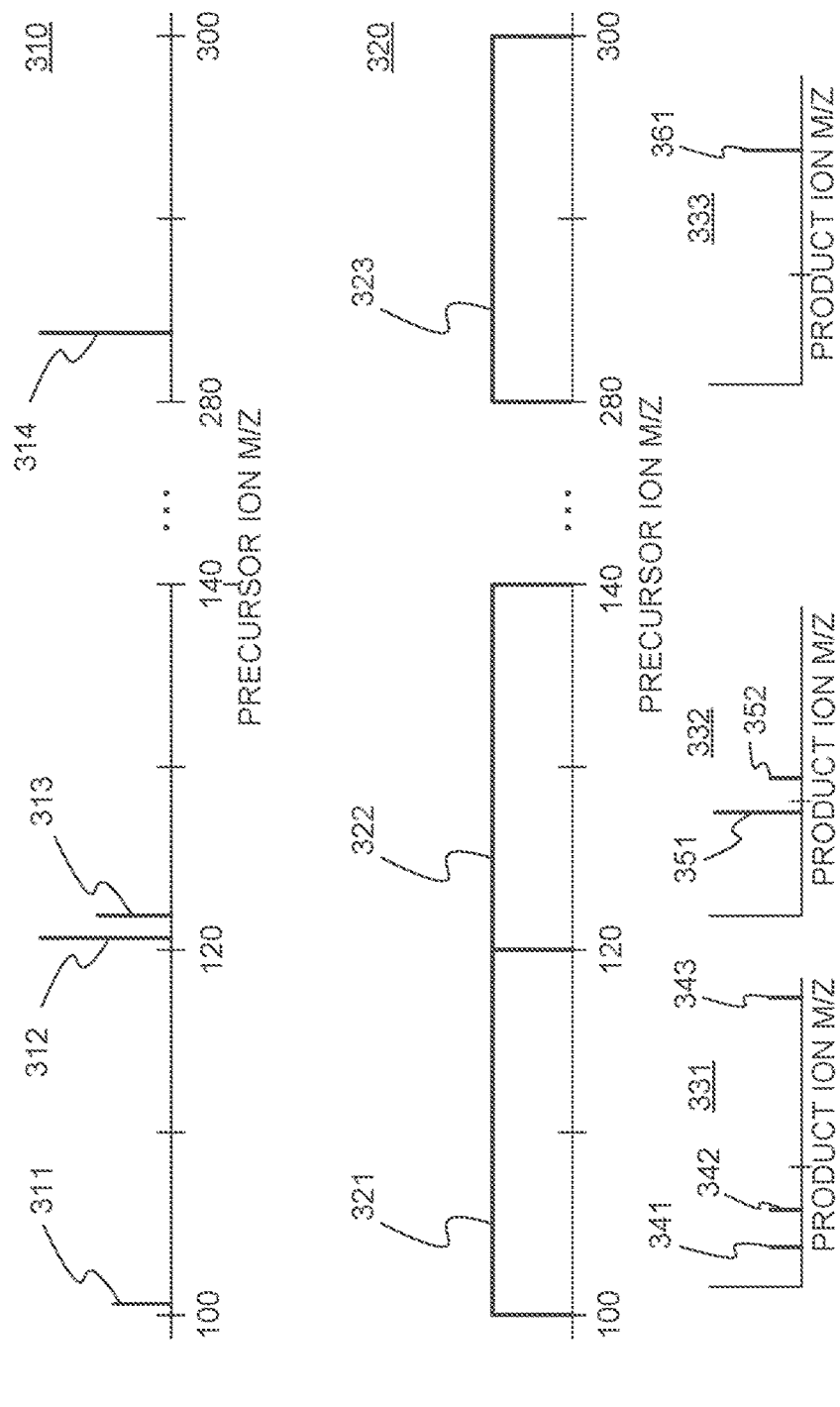
FIG. 3 is an exemplary series 3 of plots showing how product ions are correlated to precursor ions in conventional SWATH.

FIG. 3 is an exemplary series 300 of plots showing how product ions are correlated to precursor ions in conventional SWATH. Plot 310 shows a precursor ion mass range from 100 m/z to 300 m/z. When this precursor ion mass range is mass filtered and analyzed using a precursor ion scan, the precursor ion mass spectrum shown in plot 310 is found. The precursor ion mass spectrum includes precursor ion peaks 311, 312, 313, and 314, for example.

In conventional SWATH acquisition, a series of precursor ion mass selection windows, like precursor ion mass selection window 210 of FIG. 2, are selected across a precursor ion mass range. For example, ten precursor ion mass selection windows each of width 20 m/z can be selected for the precursor ion mass range from 100 m/z to 300 m/z shown in plot 310 of FIG. 3. Plot 320 shows three of the 10 precursor ion mass selection windows, 321, 322, and 323, for the precursor ion mass range from 100 m/z to 300 m/z. Note that the precursor ion mass selection windows of plot 320 do not overlap. In other conventional SWATH scans the precursor ion mass selection windows can overlap.

For each conventional SWATH scan, the precursor ion mass selection windows are sequentially fragmented and mass analyzed. As a result, for each scan, a product ion spectrum is produced for each precursor ion mass selection window. Plot 331 is the product ion spectrum produced for precursor ion mass selection window 321 of plot 320. Plot 332 is the product ion spectrum produced for precursor ion mass selection window 322 of plot 320. And, plot 333 is the product ion spectrum produced for precursor ion mass selection window 323 of plot 320.

The product ions of a conventional SWATH are correlated to precursor ions by locating the precursor ion mass selection window of each product ion, and determining the precursor ions of the precursor ion mass selection window from the precursor ion spectrum obtained from a precursor ion scan. For example, product ions 341, 342, and 343 of plot 331 are produced by fragmenting precursor ion mass selection window 321 of plot 320. Based on its location in the precursor ion mass range and the results from a precursor ion scan, precursor ion mass selection window 321 is known to include precursor ion 311 of plot 310. Since precursor ion 311 is the only precursor ion in precursor ion mass selection window 321 of plot 320, product ions 341, 342, and 343 of plot 331 are correlated to precursor ion 311 of plot 310.

Similarly, product ion 361 of plot 333 is produced by fragmenting precursor ion mass selection window 323 of plot 320. Based on its location in the precursor ion mass range and the results from a precursor ion scan, precursor ion mass selection window 323 is known to include precursor ion 314 of plot 310. Since precursor ion 314 is the only precursor ion in precursor ion mass selection window 323 of plot 320, product ion 361 is correlated to precursor ion 314 of plot 310.

The correlation, however, becomes more difficult when a precursor ion mass selection window includes more than one precursor ion and those precursor ions may produce the same or a similar product ion. In other words, when interfering precursor ions occur in the same precursor ion mass selection window, it is not possible to correlate the common product ions to the interfering precursor ions without additional information.

For example, product ions 351 and 352 of plot 332 are produced by fragmenting precursor ion mass selection window 322 of plot 320. Based on its location in the precursor ion mass range and the results from a precursor ion scan, precursor ion mass selection window 322 is known to include precursor ions 312 and 313 of plot 310. As a result, product ions 351 and 352 of plot 332 can be from precursor ion 312 or 313 of plot 310. Further, precursor ions 312 and 313 may both be known to produce a product ion at or near the m/z of product ion 351. In other words, both precursor ions may provide contributions to product ion peak 351. As a result, the correlation of a product ion to a precursor ion or to a specific contribution from a precursor ion is made more difficult.

In conventional SWATH acquisition, chromatographic peaks, such as LC peaks, can also be used to improve the correlation. In other words, the compound of interest is separated over time and the SWATH acquisition is performed at a plurality of different elution or retention times. The retention times and/or the shapes of product and precursor ion chromatographic peaks are then compared to enhance the correlation. Unfortunately, however, because the sensitivity of the precursor ion scan is low, the chromatographic peaks of precursor ions may be convolved, further confounding the correlation.

In various embodiments, scanning SWATH provides additional information that is similar to that provided by chromatographic peaks, but with enhanced sensitivity. In scanning SWATH, overlapping precursor ion mass selection windows are used to correlate precursor and product ions. For example, a single precursor ion mass selection window such as precursor ion mass selection window 210 of FIG. 2 is shifted in small steps across a precursor mass range so that there is a large overlap between successive precursor ion mass selection windows. As the amount of overlap between precursor ion mass selection windows is increased, the accuracy in correlating the product ions to precursor ions is also increased.

Essentially, when the intensities of product ions produced from precursor ions filtered by the overlapping precursor ion mass selection windows are plotted as a function of the precursor ion mass selection window moving across the precursor mass range, each product ion has an intensity for the same precursor mass range that its precursor ion has been transmitted. In other words, for a rectangular precursor ion mass selection window (such as precursor ion mass selection window 210 of FIG. 2) that transmits precursor ions at a constant rate with respect to precursor mass, the edges (such as edges 220 and 230 of FIG. 2) define a unique boundary of both precursor ion precursor ion mass selection and product ion intensity as the precursor ion mass selection is stepped across the precursor mass range.

Figure 4:
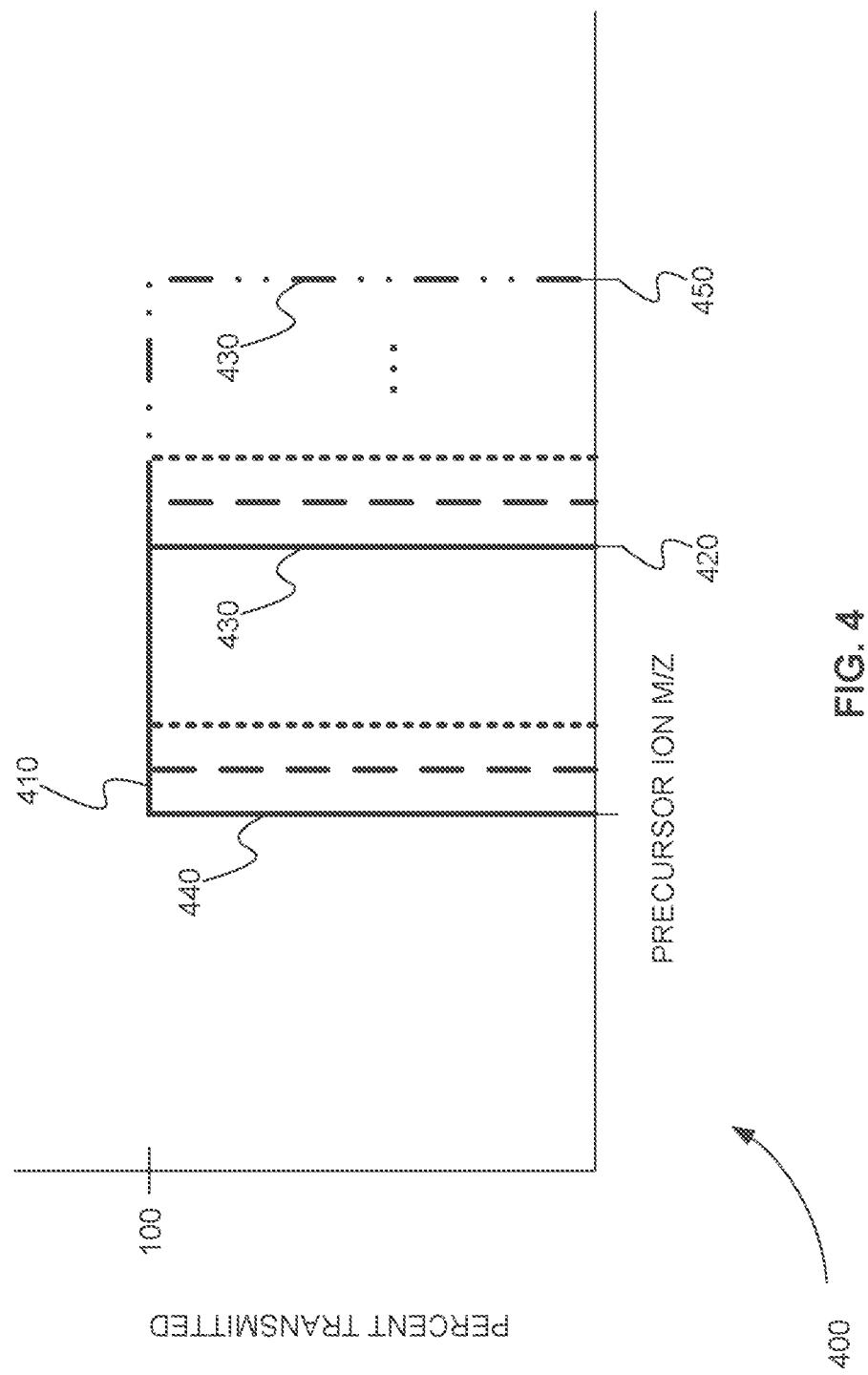
FIG. 4 is an exemplary plot of a precursor ion mass selection window that is shifted or scanned across a precursor ion mass range in order to produce overlapping precursor ion mass selection windows, in accordance with various embodiments.

FIG. 4 is an exemplary plot 400 of a precursor ion mass selection window 410 that is shifted or scanned across a precursor ion mass range in order to produce overlapping precursor ion mass selection windows, in accordance with various embodiments. Precursor ion mass selection window 410, for example, starts to transmit precursor ion with m/z value 420 when leading edge 430 reaches precursor ion with m/z value 420. As precursor ion mass selection window 410 is shifted across the m/z range, the precursor ion with m/z value 420 is transmitted until trailing edge 440 reaches m/z value 420.

When the intensities of the product ions from the product ion spectra produced by the overlapping windows are plotted, for example, as a function of the m/z value of leading edge 430, any product ion produced by the precursor ion with m/z value 420 would have an intensity between m/z value 420 and m/z value 450 of leading edge 430. One skilled in the art can appreciate that the intensities of the product ions produced by the overlapping windows can be plotted as a function of the precursor ion m/z value based on any parameter of precursor ion mass selection window 410 including, but not limited to, trailing edge 440, set mass, center of gravity, or leading edge 430.

Figure 5:
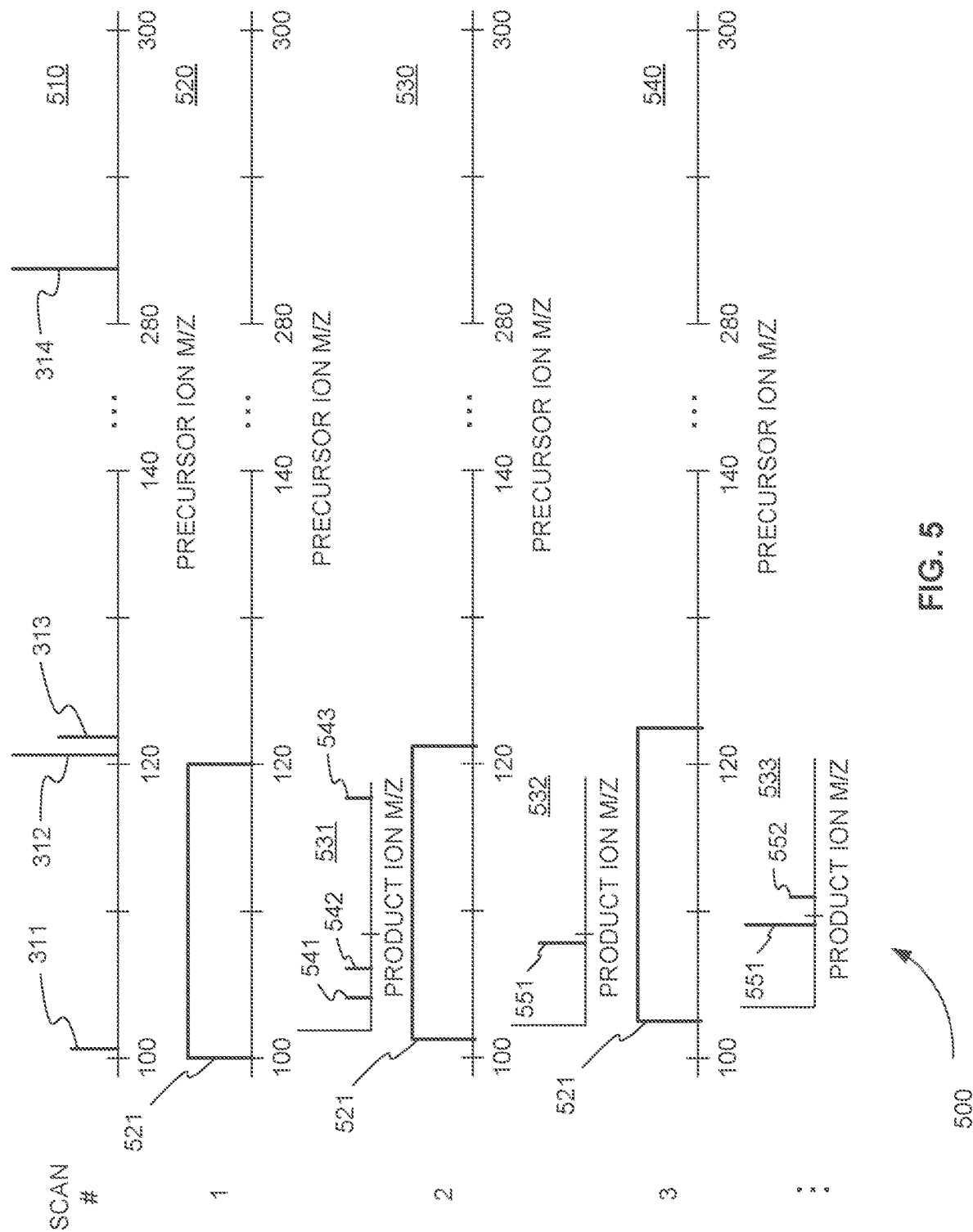
FIG. 5 is an exemplary series of plots showing how product ions are correlated to precursor ions in scanning SWATH, in accordance with various embodiments.

FIG. 5 is an exemplary series 500 of plots showing how product ions are correlated to precursor ions in scanning SWATH, in accordance with various embodiments. Plot 510 is the same as plot 310 of FIG. 3. Plot 510 of FIG. 5 shows a precursor ion mass range from 100 m/z to 300 m/z. When this precursor ion mass range is mass filtered and analyzed using a precursor ion scan, the precursor ion mass spectrum shown in plot 510 is found. The precursor ion mass spectrum includes precursor ion peaks 311, 312, 313, and 314, for example.

In scanning SWATH, however, rather than selecting and then fragmenting and mass analyzing non-overlapping precursor ion mass selection windows across the mass range, a precursor ion mass selection window is quickly moved or scanned across the precursor ion mass range with large overlaps between windows in each scanning SWATH scan. For example, during scan 1, precursor ion mass selection window 521 of plot 520 extends from 100 m/z to 120 m/z. The fragmentation of precursor ion mass selection window 521 and mass analysis of the resulting fragments during scan 1 produces the product ions of plot 531. Product ions 541, 542, and 543 of plot 531 are known to correlate to precursor ion 311 of plot 510, because precursor ion 311 is the only precursor within precursor ion mass selection window 521 of plot 520. Note that plot 531 includes the same product ions as plot 331 of FIG. 3.

For scan 2, precursor ion mass selection window 521 is shifted 1 m/z as shown in plot 530. Precursor ion mass selection window 521 of plot 530 no longer includes precursor ion 311 of plot 510. However, precursor ion mass selection window 521 of plot 530 now includes precursor ion 312 of plot 510. The fragmentation of precursor ion mass selection window 521 and mass analysis of the resulting fragments during scan 2 produces the product ion of plot 532. Product ion 551 of plot 532 is known to correlate to precursor ion 312 of plot 510, because precursor ion 312 is the only precursor within precursor ion mass selection window 521 of plot 530. Note that product ion 551 of plot 532 has the same m/z value as product ion 351 of plot 332 of FIG. 3, but a different intensity. From plot 532 of FIG. 5, it is now known what portion of 351 of plot 332 of FIG. 3 is from precursor ion 312 of plot 510.

For scan 3, precursor ion mass selection window 521 is shifted another 1 m/z as shown in plot 540. Precursor ion mass selection window 521 of plot 540 now includes precursor ions 312 and 313 of plot 510. The fragmentation of precursor ion mass selection window 521 and mass analysis of the resulting fragments during scan 3 produces the product ions of plot 533. Because precursor ion mass selection window 521 of plot 540 includes precursor ions 312 and 313 of plot 510, product ions 551 and 552 of plot 533 can be from either or both precursor ions.

Note that plot 533 includes the same product ions as plot 332 of FIG. 3. However, due to the additional information from scanning SWATH correlation is now possible. As mentioned above, from plot 532 of FIG. 5, it is now known what portion of 351 of plot 332 of FIG. 3 is from precursor ion 312 of plot 510. In other words, when the leading edges of precursor ion mass selection window 521 reaches precursor ion 312 of plot 510 and the trailing edges of precursor ion mass selection window 521 no longer includes precursor ion 312 of plot 510, the contribution of precursor ion 312 of plot 510 is known.

In addition, comparing plots 532 and 533 of FIG. 5 determines the contributions of precursor ion 313 of plot 510. Note that once the leading edge of precursor ion mass selection window 521 reaches precursor ion 313 of plot 510, product ion 552 of plot 533 appears and the intensity of product ion 551 increases. Thus product ion 552 is correlated to precursor ion 313 of plot 510 and the additional intensity of product ion 551 is also correlated to precursor ion 313 of plot 510.

Figure 6:
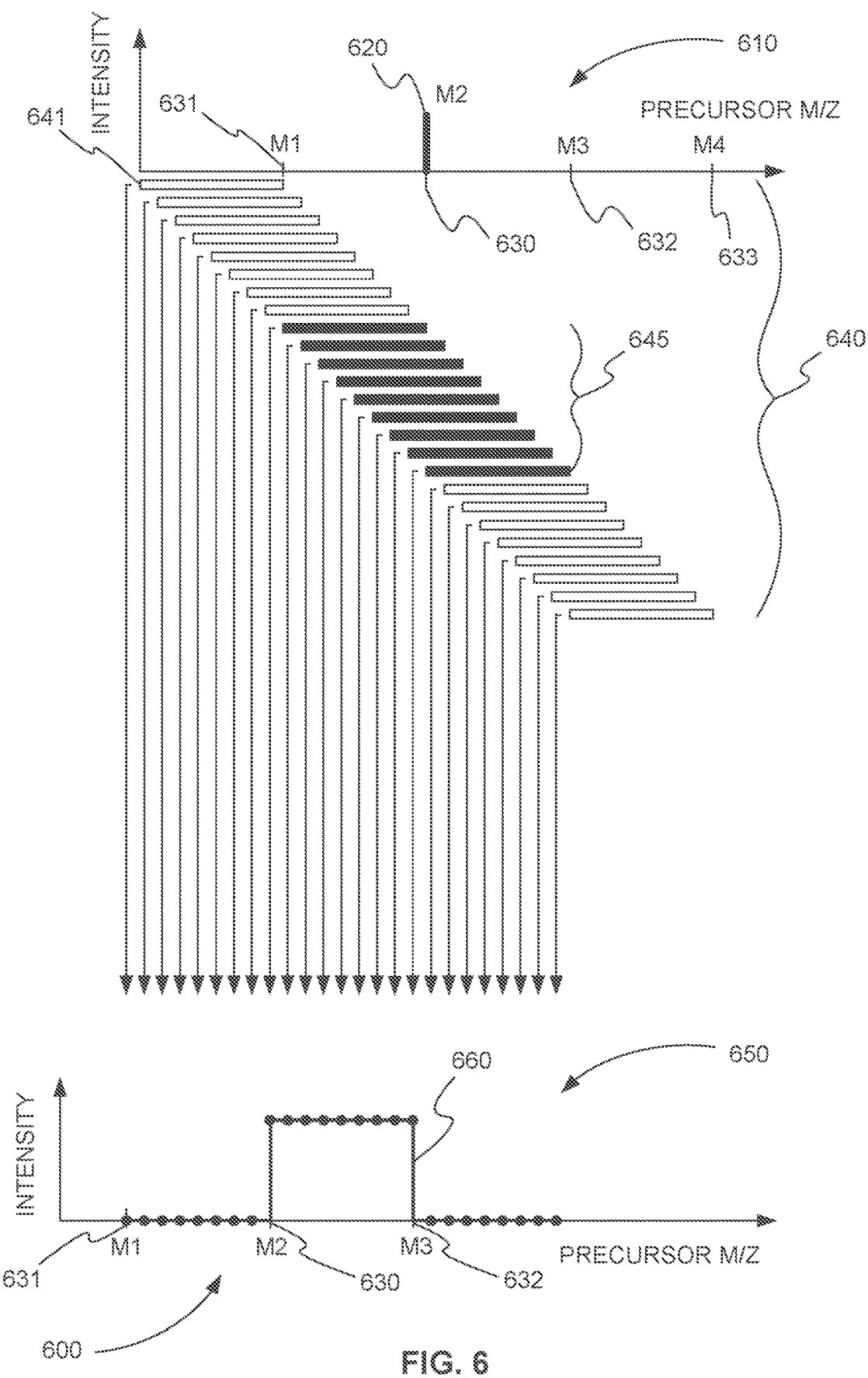
FIG. 6 is a diagram showing how a product ion produced from a precursor ion that is filtered by overlapping precursor ion mass selection windows in a scanning SWATH acquisition can be plotted as a function of the precursor ion mass selection window moving across the precursor mass range, in accordance with various embodiments.

FIG. 6 is a diagram 600 showing how a product ion produced from a precursor ion that is filtered by overlapping precursor ion mass selection windows in a scanning SWATH acquisition can be plotted as a function of the precursor ion mass selection window moving across the precursor mass range, in accordance with various embodiments. Plot 610 shows that there is a precursor ion 620 at m/z 630. Precursor ion mass selection window 641 is stepped across the precursor ion mass range from m/z 631 to m/z 633, resulting in overlapping rectangular precursor ion mass selection windows 640. Each window of precursor ion mass selection windows 640 is fragmented. The resulting product ions are then mass analyzed, producing a product ion mass spectrum (not shown) for each window of precursor ion mass selection windows 640.

FIG. 6 shows just one scan of precursor ion mass selection window 641 across precursor ion mass range from m/z 631 to m/z 633. However, precursor ion mass selection window 641 can be scanned across precursor ion mass range from m/z 631 to m/z 633 multiple times, for example.

A product ion is selected from one of the product ion spectra produced. A product ion is selected, for example, that has a mass peak above a certain threshold.

The intensity of the product ion is then calculated as a function of the position of precursor ion mass selection window 641 by obtaining the intensity of the product ion from each product ion spectrum produced for each precursor ion mass selection window of precursor ion mass selection windows 640. The intensity of a selected product ion calculated as a function of the position of the precursor ion mass selection window can be called, for example, a quadrupole ion trace (QIT).

An exemplary QIT 660 calculated for a product ion is shown in plot 650. QIT 660 shows the intensities of the selected product ion obtained from each product ion spectrum produced for each precursor ion mass selection window of precursor ion mass selection windows 640. The intensities are plotted as a function of the leading edge of precursor ion mass selection windows 640. However, as described above, these intensities can be plotted as a function of any parameter of precursor ion mass selection windows 640 including, but not limited to, the trailing edge, set mass, leading edge, or scan time.

QIT 660 of plot 650 shows that the intensity of the selected product ion becomes non-zero when the leading edge of scanning precursor ion mass selection window 641 reaches m/z 630. It also shows that the intensity of the product ion returns to zero when the leading edge of the scanning precursor ion mass selection window passes m/z 632. In other words, QIT 660 has sharp leading and trailing edges corresponding to locations of scanning precursor ion mass selection window 641.

FIG. 6, shows that the leading and trailing edges of QIT 660 can be used to determine the corresponding precursor ion of the selected product ion. Essentially, the leading and trailing edges of QIT 660 mean that the precursor ion of the selected product ion must be in the precursor ion mass selection windows between these edges. Precursor ion mass selection windows 645 of precursor ion mass selection windows 640 have leading edges within these windows. Plot 610 shows that precursor ion 620 is the only precursor ion that can be in precursor ion mass selection windows 645. Therefore, the selected product ion with QIT 660 corresponds to precursor ion 620.

This leading and trailing edge analysis of a QIT was described in the '459 application. Unfortunately, there are two problems with this type of analysis. First, as the '066 application describes, most mass filters are unable to produce precursor ion mass selection windows with sharply defined edges. As a result, a calculated QIT is likewise unlikely to have sharply defined edges. Secondly, the product ion may be a result of two or more different precursor ions that have similar masses. In other words, the product ion intensity may be a convolution intensities produced from two or more interfering precursor ions.

Figure 7:
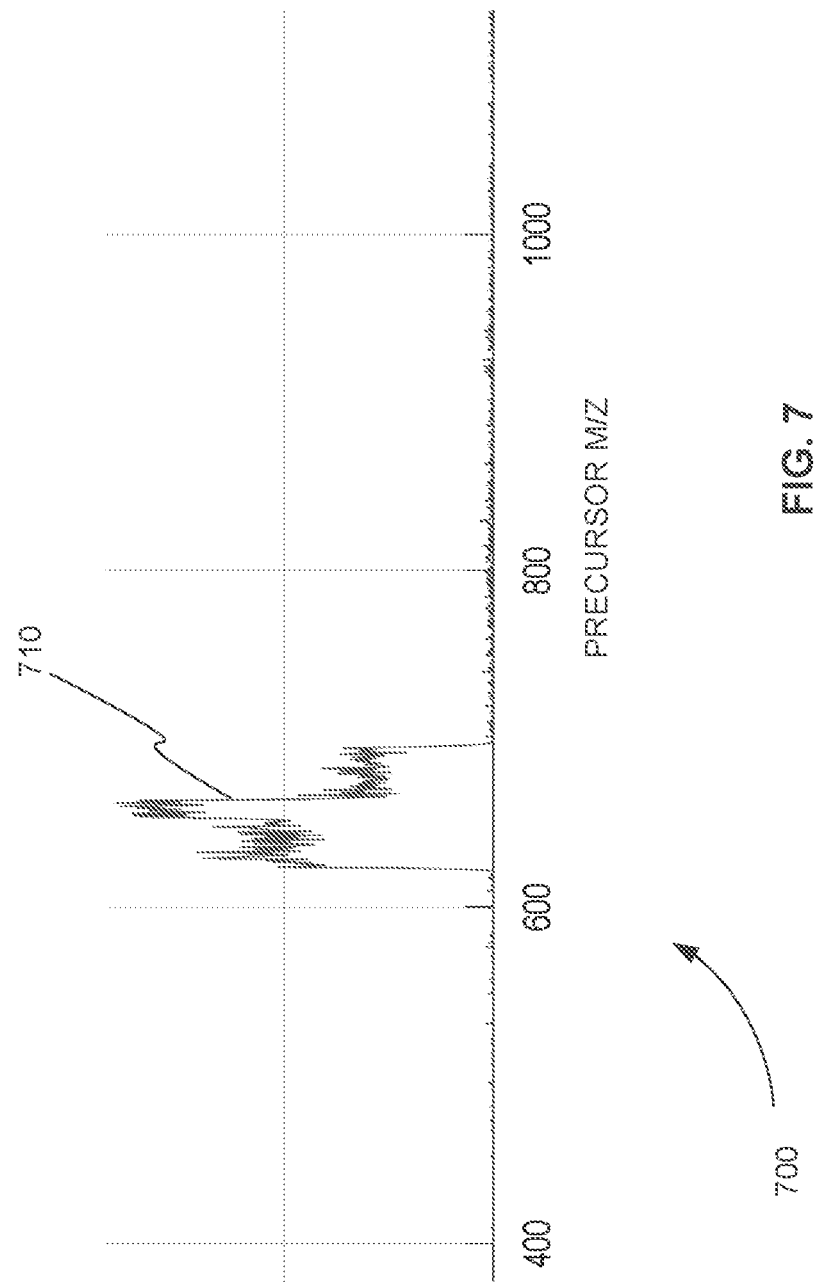
FIG. 7 is a plot of an exemplary quadrupole ion trace (QIT) calculated for a selected product ion that is produced from two interfering precursor ions using data from an actual scanning SWATH experiment, in accordance with various embodiments.

FIG. 7 is a plot 700 of an exemplary quadrupole ion trace (QIT) calculated for a selected product ion that is produced from two interfering precursor ions using data from an actual scanning SWATH experiment, in accordance with various embodiments. A comparison of plot 700 with plot 650 of FIG. 6 shows that an actual QIT does not have sharply defined edges. The comparison also shows the multiple levels of intensities caused by the two interfering precursor ions further complicates the determination of the corresponding precursor ions. As a result, methods other than simple edge detection are needed to accurately determine the corresponding precursor ions from a product ion QIT.

In various embodiments, the corresponding precursor ions are determined from a product ion QIT using a system of linear equations. For example, each step of the precursor ion mass selection window across the mass range is represented by a linear equation. The unknown variables of each linear equation are the intensities of the precursor ion m/z values across the precursor ion mass range. The coefficients of each linear equation specify the position of the precursor ion mass selection window. The result of each equation is the value of the QIT at that particular step of the precursor ion mass selection window across the mass range. The corresponding precursor ions of a product ion QIT are found by solving the system of linear equations for the precursor ion intensity values across the precursor ion mass range (the unknown variables).

In various embodiments, the system of linear equations used to determine the corresponding precursor ions of a product ion QIT is represented as a matrix multiplication equation. For example, an n×m matrix is multiplied by a column matrix of length m producing a column matrix of length n. The n×m matrix represents the mass filter. The rows, n, are the locations of the precursor ion mass selection window across the precursor ion mass range. The columns, m, are the precursor ion m/z values across the precursor ion mass range. The elements of the n×m matrix represent the transmission (1) or non-transmission (0) by the precursor ion mass selection window at that location and precursor ion m/z value. The elements are known from the acquisition. This is how the mass filter scans the precursor ion mass selection window across the precursor ion mass range.

The rows, m, of the column matrix of length m correspond to the columns of the n×m matrix and are the precursor ion m/z values across the precursor ion mass range. The elements of the column matrix of length m are the intensities of the precursor ions at the precursor ion m/z value. These elements are unknown.

The rows, n, of the column matrix of length n correspond to the rows of the n×m matrix and are the locations of the precursor ion mass selection window across the precursor ion mass range. The elements of the column matrix of length n are the intensities of the product ion at locations of the precursor ion mass selection window across the precursor ion mass range that are known from the QIT calculated for a particular acquisition.

Figure 8:
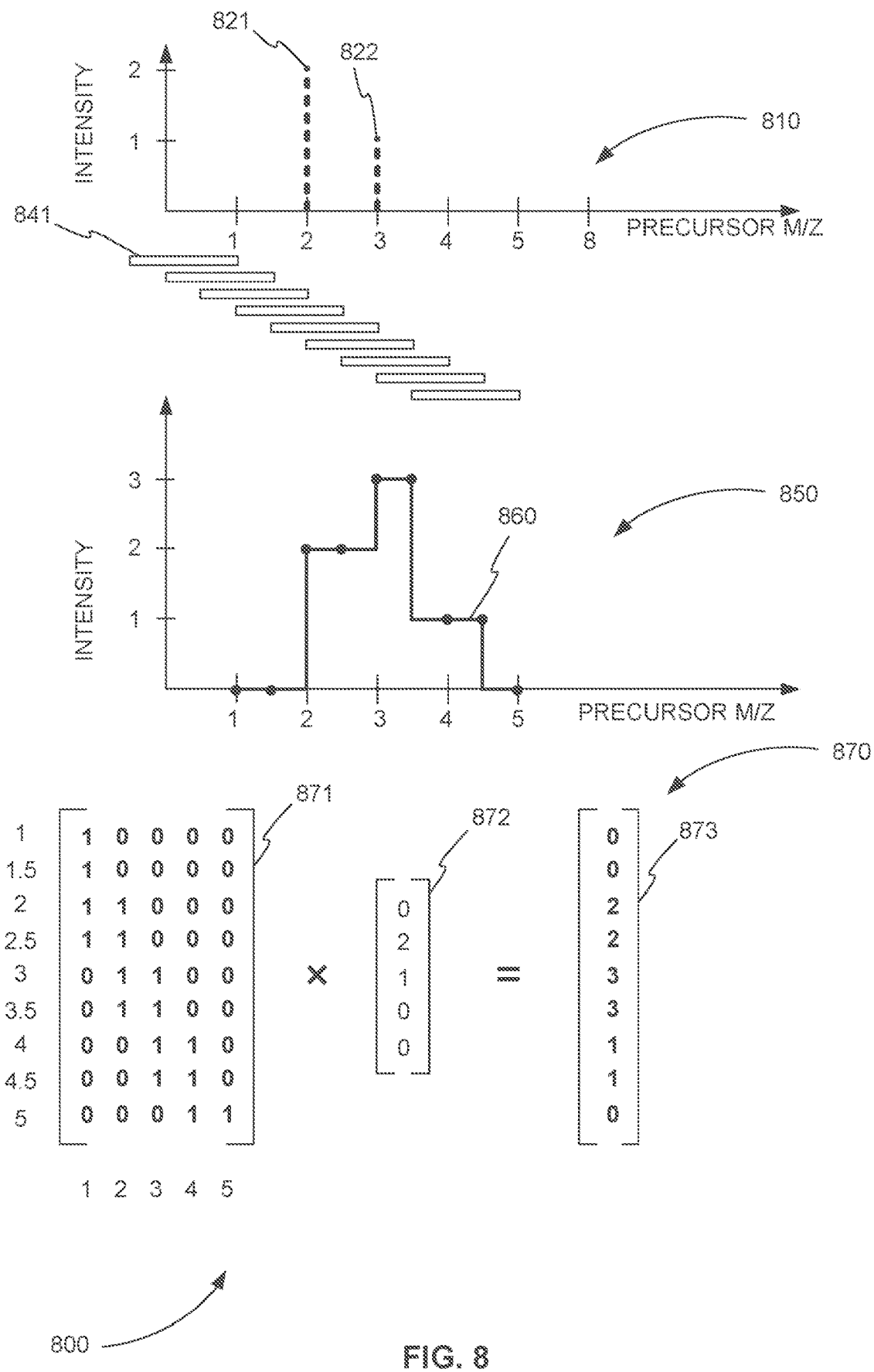
FIG. 8 is a diagram showing a simplified example of how corresponding precursor ions are determined from a product ion QIT using a system of linear equations represented by a matrix multiplication equation, in accordance with various embodiments.

FIG. 8 is a diagram 800 showing a simplified example of how corresponding precursor ions are determined from a product ion QIT using a system of linear equations represented by a matrix multiplication equation, in accordance with various embodiments. Plot 810 shows how precursor ion mass selection window 841 is scanned across a precursor ion mass range from an m/z of 1 to an m/z of 5. Precursor ions 821 and 822 are unknown.

A product ion is selected from the product ion spectra produced from scanning precursor ion mass selection window 841 across the precursor ion mass range from an m/z of 1 to an m/z of 5, fragmenting each window, and mass analyzing the product ions produced for each window. QIT 860 of plot 850 is the QIT calculated for the selected product ion. As described above, the actual QIT of the selected product ion will not have the sharp edges of QIT 860. In fact, the actual QIT of the selected product ion will look much more like QIT 510 of FIG. 5. However, QIT 860 is drawn with sharp edges to simplify the example.

In order to determine the precursor ions corresponding to QIT 860 a system of linear equations is calculated. This system is represented in the form of matrix multiplication equation 870. In equation 870, 9×5 mass filter matrix 871 is multiplied by precursor ion column matrix 872 of length 5 producing QIT column matrix 873 of length 9. The elements of mass filter matrix 871 are known from movements of precursor ion mass selection window 841 during the scan across the precursor ion mass range. QIT column matrix 873 is also known. It is calculated from the product ion spectra produced. Precursor ion column matrix 872 is unknown.

In various embodiments, a numerical method is applied to matrix multiplication equation 870 to solve for precursor ion column matrix 872. The solution for precursor ion column matrix 872 determines the corresponding precursor ions for QIT 860. For example, the solution for precursor ion column matrix 872 shows that the selected product ion with QIT 860 was produced from a precursor ion with intensity 2 at 2 m/z and a precursor ion with intensity 1 at 3 m/z. These precursor ions are ions 821 and 822, respectively, shown in plot 810.

In various embodiments, the numerical method applied to matrix multiplication equation 870 is non-negative least squares (NNLS).

Figure 9:
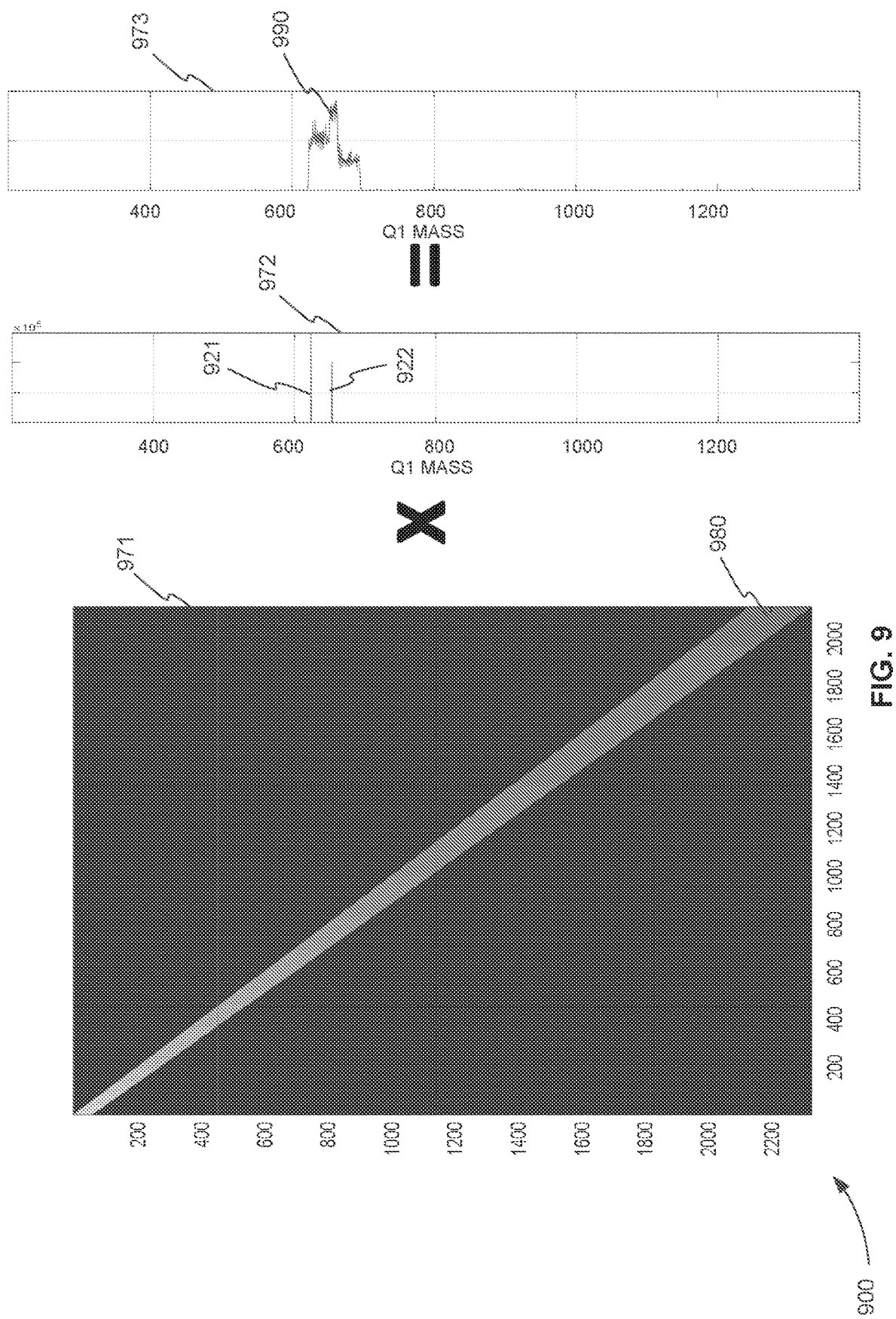
FIG. 9 is an exemplary matrix multiplication equation showing an experimental example of how corresponding precursor ions are determined from a product ion QIT, in accordance with various embodiments.

FIG. 9 is an exemplary matrix multiplication equation 900 showing an experimental example of how corresponding precursor ions are determined from a product ion QIT, in accordance with various embodiments. Matrix multiplication equation 900 includes quadrupole 1 (Q1) mass filter matrix 971, precursor ion column matrix 972, and QIT column matrix 973. Q1 mass filter matrix 971 is known from the acquisition and describes how the Q1 mass filter scan operates. Note that Q1 mass filter matrix 971 includes non-zero values along diagonal 980, corresponding to the sliding precursor ion mass selection window of scanning SWATH™.

QIT column matrix 973 includes the known or observed product ion intensities of the selected product ion as a function of Q1 or precursor ion mass or m/z. QIT column matrix 973 is represented in FIG. 9 by actual calculated QIT 990.

Precursor ion column matrix 972 is the unknown. Matrix multiplication equation 900 is solved for precursor ion column matrix 972. Precursor ion column matrix 972 includes the intensities of the precursor ions corresponding to the product ion for which QIT column matrix 973 is calculated. Precursor ion column matrix 972 is represented in FIG. 9 by a precursor ion spectrum that can be produced from precursor ion column matrix 972. When matrix multiplication equation 900 is solved, precursor ions 921 and 922 are found to correspond to QIT 990. Matrix multiplication equation 900 is solved using the NNLS numerical method.

Improvement Over Other Methods

Figure 10:
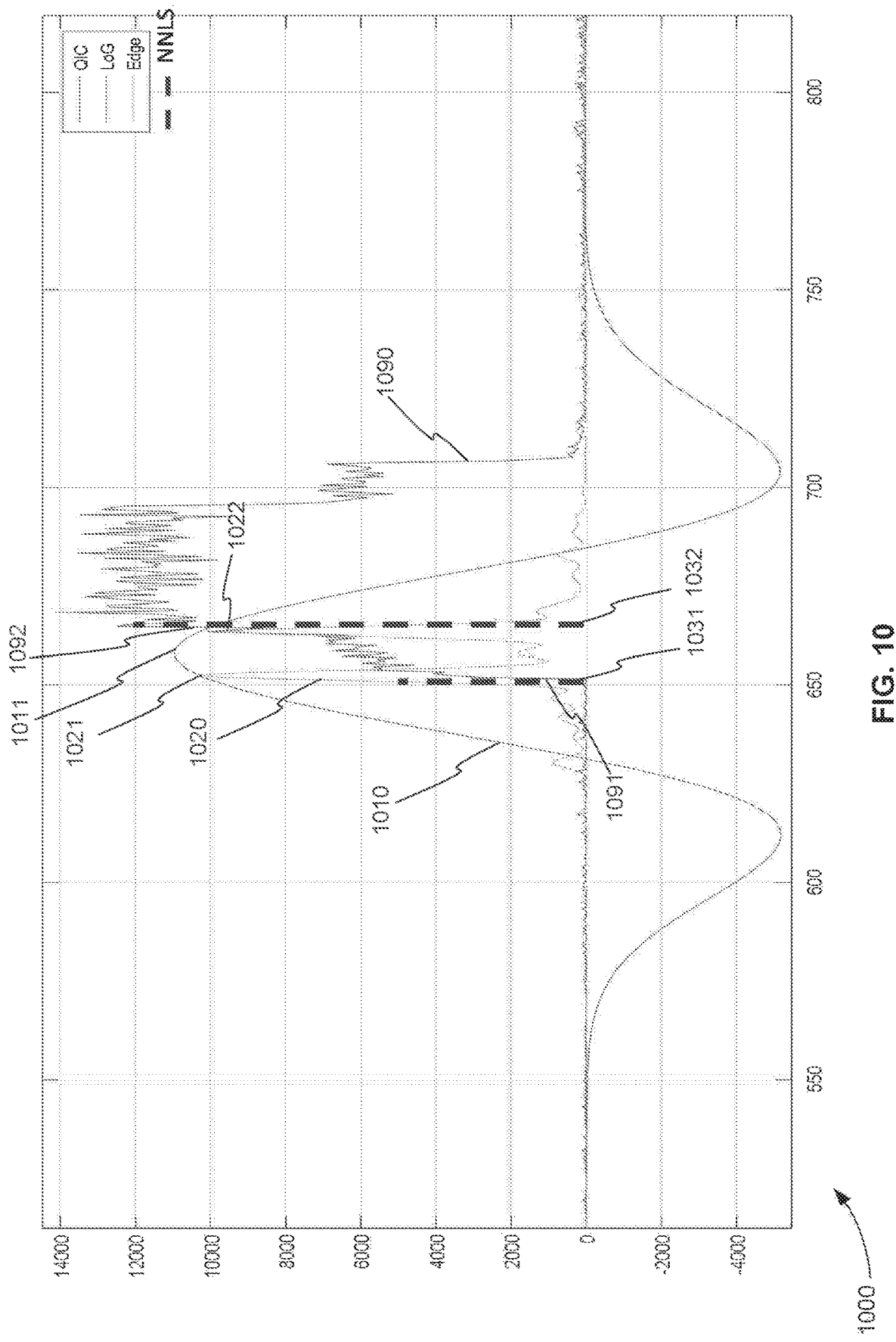
FIG. 10 is an exemplary plot of the results of three numerical methods used to determine the corresponding precursor ions of a selected product ion superimposed on the calculated QIT of the selected product ion, in accordance with various embodiments.

FIG. 10 is an exemplary plot 1000 of the results of three numerical methods used to determine the corresponding precursor ions of a selected product ion superimposed on the calculated QIT of the selected product ion, in accordance with various embodiments. In Plot 1000, QIT 1090 is the QIT for the selected product ion that is calculated from the scanning SWATH™ product ion spectra for a single scan of the precursor ion mass range. Generally, in a QIT, rising edges correspond to precursor ion masses or m/z values. Falling edges correspond to precursor ion masses or m/z values plus the precursor ion mass selection window width. QIT 1090 includes multiple rising edges (two), which suggests that there are interfering precursors (two). As a result, the product ion is a convolution of the contributions from two precursor ions.

Waveform 1010 represents the result from performing a Laplacian of Gaussian (LoG) or Mexican Hat numerical method on QIT 1090. Waveform 1020 represents the result from performing an edge detection numerical method on QIT 1090. Lines 1031 and 1032 represent the results from performing an NNLS method applied to a matrix multiplication equation that includes QIT 1090.

A comparison of these three results shows that waveform 1010 of the LoG is not specific enough for a convolved product ion. In other words, LoG is not able to find multiple precursor ions. Waveform 1010 only has a single peak 1011. In contrast, waveform 1020 of the edge detection numerical method is able to detect two precursor ions at peaks 1021 and 1022. Similarly, lines 1031 and 1032 of the NNLS method are able to detect two precursor ions.

Although the edge detection numerical method and the NNLS method are able to detect two precursor ions, the NNLS method provides a more accurate or more specific calculation of the rising edges of QIT 1090. For example, peak 1021 of waveform 1020 has a higher m/z than the actual first rising edge 1091 of QIT 1090. In contrast, line 1031 of the NNLS method appears to be closer to the actual first rising edge 1091 of QIT 1090. Even more telling is the difference in the detection of second rising edge 1092 of QIT 1090. Peak 1022 of waveform 1020 has a significantly lower m/z value than the actual second rising edge 1092 of QIT 1090. In contrast, line 1032 of the NNLS method appears to be closer to the actual second rising edge 1092 of QIT 1090.

In summary, applying an NNLS method to a matrix multiplication equation to determine corresponding precursor ion, as described in various embodiments of the present application, provides a significant improvement over current methods such as LoG or edge detection. The NNLS method is particularly advantageous in the case of multiple interfering precursor ions.

System for Identifying a Precursor Ion from a Product Ion

Figure 11:
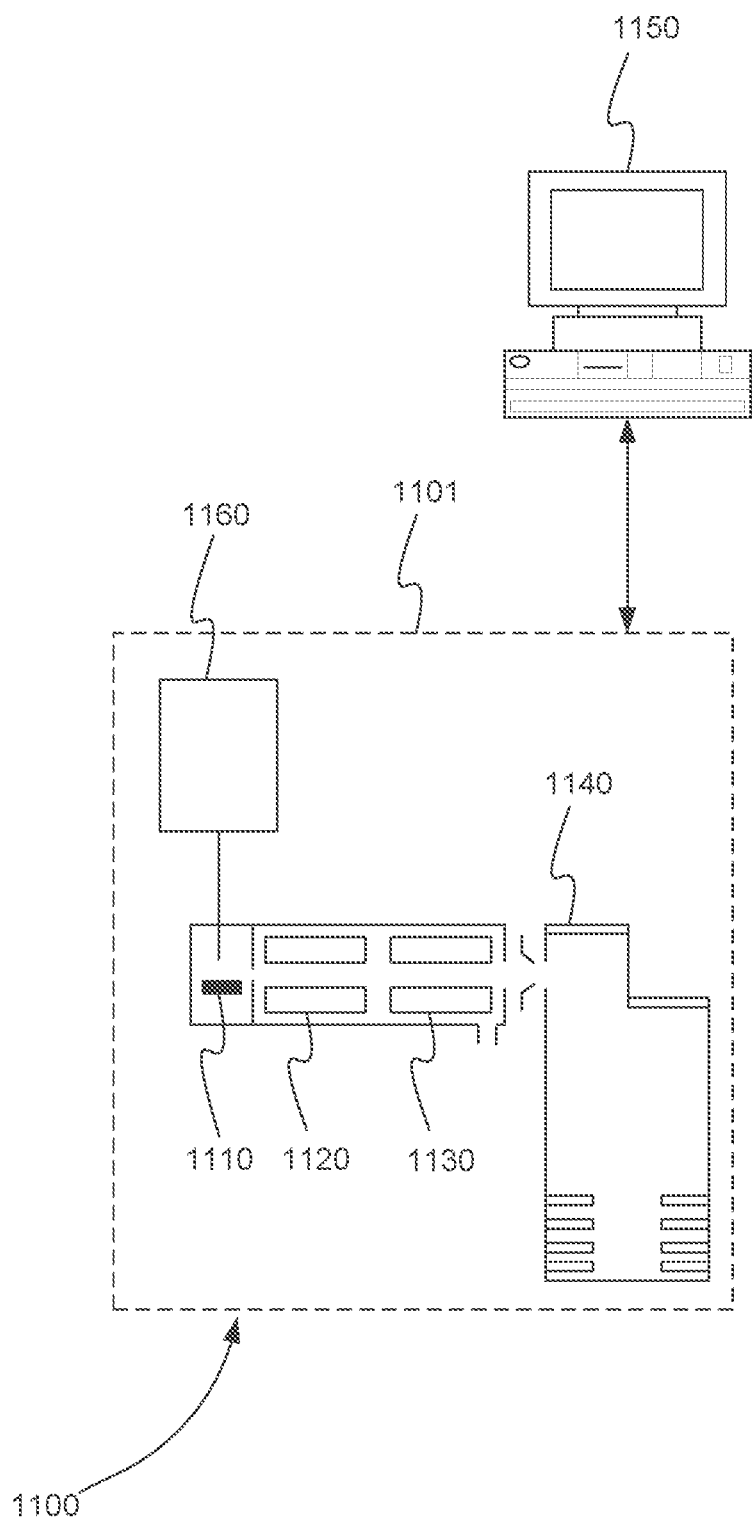
FIG. 11 is a schematic diagram showing a system for identifying a precursor ion of a product ion in a scanning data-independent acquisition (DIA) tandem mass spectrometry experiment, in accordance with various embodiments.

FIG. 11 is a schematic diagram 1100 showing a system 1101 for identifying a precursor ion of a product ion in a scanning DIA tandem mass spectrometry experiment, in accordance with various embodiments. System 1101 of FIG. 11 includes ion source device 1110, mass filter 1120, fragmentation device 1130, mass analyzer 1140, and processor 1150.

In various embodiments, system 1101 can further include sample introduction device 1160. Sample introduction device 1160 introduces one or more compounds of interest from a sample to ion source device 1110 over time, for example. Sample introduction device 1160 can perform techniques that include, but are not limited to, injection, liquid chromatography, gas chromatography, capillary electrophoresis, or ion mobility.

In system 1101, mass filter 1120 and fragmentation device 1130 are shown as different stages of a quadrupole and mass analyzer 1140 is shown as a time-of-flight (TOF) device. One of ordinary skill in the art can appreciate that any of these stages can include other types of mass spectrometry devices including, but not limited to, ion traps, orbitraps, ion mobility devices, or Fourier transform ion cyclotron resonance (FT-ICR) devices.

Ion source device 1110 transforms a sample or compounds of interest from a sample into an ion beam. Ion source device 1110 can perform ionization techniques that include, but are not limited to, matrix assisted laser desorption/ionization (MALDI) or electrospray ionization (ESI).

Mass filter 1120 receives the ion beam. Mass filter 1120 then filters the ions by scanning a precursor ion mass selection window across a precursor ion mass range of interest. As a result, a series of overlapping precursor ion mass selection windows across the precursor ion mass range are produced.

Fragmentation device 1130 receives the precursor ions of each overlapping precursor ion mass selection window. Fragmentation device 1130 then fragments the precursor ions of each overlapping precursor ion mass selection window.

Mass analyzer 1140 receives the product ions from each fragmentation of each overlapping precursor ion mass selection window. Mass analyzer 1140 then analyzes the resulting product ions, producing a product ion spectrum for each overlapping precursor ion mass selection window and a plurality of product ion spectra for the precursor ion mass range.

Processor 1150 can be, but is not limited to, a computer, a microprocessor, the computer system of FIG. 1, or any device capable of sending and receiving control signals and data from a tandem mass spectrometer and processing data. Processor 1150 is in communication with ion source device 1110, mass filter 1120, fragmentation device 1130, and mass analyzer 1140.

Processor 1150 receives the plurality of product ion spectra produced by the series of overlapping precursor ion mass selection windows from mass analyzer 1140. Processor 1150 selects at least one product ion from the plurality of product ion spectra that has an intensity above a predetermined threshold. For the selected product ion, processor 1150 retrieves the intensities of the selected product ion from the plurality of product ion spectra for at least one scan of the precursor ion mass selection window across the precursor ion mass range. These intensities produce a trace that describes how the intensity of the selected product ion varies with precursor ion mass-to-charge ratio (m/z) as the precursor ion mass selection window is scanned across the precursor ion mass range.

Processor 1150 creates a matrix multiplication equation that describes how one or more precursor ions correspond to the trace for the selected product ion. The matrix multiplication equation includes a known n×m mass filter matrix multiplied by an unknown precursor ion column matrix of length m that equates to a selected ion trace column matrix of length n.

Finally, processor 1150 solves the matrix multiplication equation for the unknown precursor ion column matrix using a numerical method. The solution produces intensities for one or more precursor ion m/z values corresponding to the selected product ion.

In various embodiments, processor 1150 solves the matrix multiplication equation using non-negative least squares (NNLS) method.

As described above, processor 1150 selects at least one product ion from the plurality of product ion spectra that has an intensity above a predetermined threshold. One of skill in the art can appreciate that selecting at least one product ion from the plurality of product ion spectra can also be described as selecting one product ion bin. A bin is, for example, the smallest product ion mass range that is detectable by the detector of mass analyzer 1140.

In various embodiments, processor 1150 can select more than one product ion bin and calculate intensities for one or more precursor ion m/z values corresponding to the more than one product ion bins. In addition, in various embodiments, processor 1150 can all the product ion bins and calculate intensities for one or more precursor ion m/z values corresponding to each of the product ion bins.

In various embodiments, rows, n, of the mass filter matrix are the locations of the precursor ion mass selection window across the precursor ion mass range, the columns, m, of the mass filter matrix are the precursor ion m/z values across the precursor ion mass range, and the elements of the mass filter matrix represent the transmission or non-transmission by the precursor ion mass selection window. Rows, m, of the unknown precursor ion column matrix correspond to the columns of the mass filter matrix and are the precursor ion m/z values across the precursor ion mass range, and the elements of the unknown precursor ion column matrix are the intensities of the precursor ions corresponding to the selected product ion. Rows, n, of the trace column matrix correspond to the rows of the mass filter matrix and are the locations of the precursor ion mass selection window across the precursor ion mass range, and the elements of the trace column matrix are the intensities of the selected product ion at locations of the precursor ion mass selection window across the precursor ion mass range.

In various embodiments, precursor ion information is obtained ahead of time by performing a precursor ion scan. This information is then used to aid in the identification of the precursor ion(s) corresponding to the selected product ion. For example, before filtering the ion beam by scanning a precursor ion mass selection window across a precursor ion mass range of interest, mass filter 1120 filters the ion beam for precursor ions in the precursor ion mass range of interest, producing a plurality of precursor ions. Mass analyzer 1130 then analyzes the plurality of precursor ions, producing a precursor ion spectrum. The precursor ion spectrum used is filtered from most adducts and fragments.

In various embodiments, the dimensions of the matrix multiplication equation are reduced based on the precursor ion spectrum. For example, for each precursor ion m/z value with an intensity above a precursor ion intensity threshold in the precursor ion spectrum, processor 1150 creates a possible precursor ion m/z value, producing a plurality of possible precursor ion m/z values across the precursor ion mass range. Processor 1150 then reduces columns, m, of the n×m mass filter matrix so that the columns of the mass filter matrix to correspond to the plurality of possible precursor ion m/z values.

Figure 12:
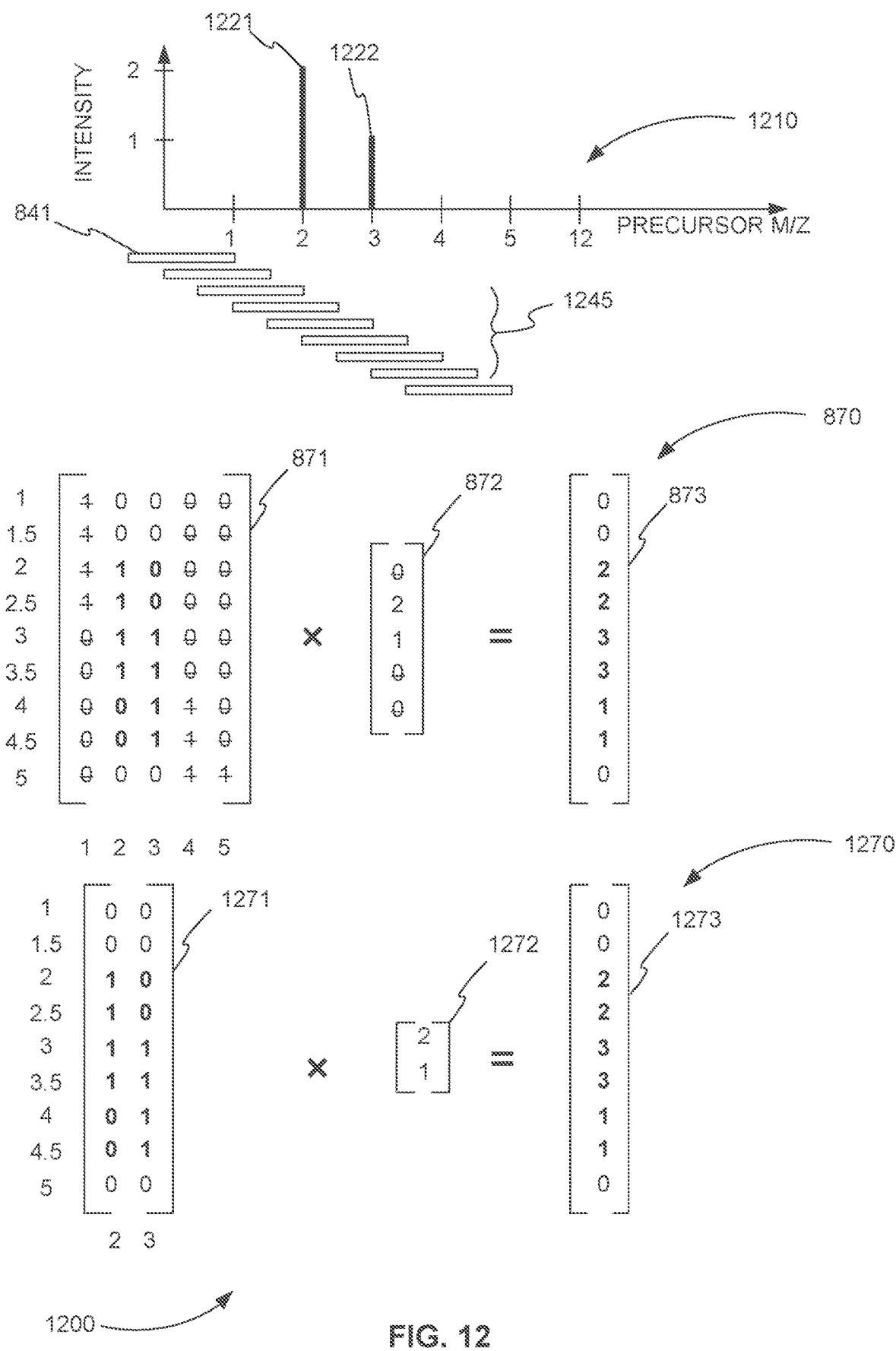
FIG. 12 is a diagram showing how the matrix multiplication equation of FIG. 8 can be reduced based on information from a precursor ion spectrum obtained before performing a scanning DIA experiment, in accordance with various embodiments.

FIG. 12 is a diagram 1200 showing how the matrix multiplication equation of FIG. 8 can be reduced based on information from a precursor ion spectrum obtained before performing a scanning DIA experiment, in accordance with various embodiments. Plot 1210 shows how precursor ion mass selection window 841 is scanned across a precursor ion mass range from an m/z of 1 to an m/z of 5 in a DIA experiment. Precursor ions 1221 and 1222, however, are now known to exist from the precursor ion scan performed before the DIA experiment. Precursor ions 1221 and 1222 are, therefore, the possible precursor ion m/z values. No other precursor ions are found above the precursor ion intensity threshold within the precursor ion mass range from an m/z of 1 to an m/z of 5.

Knowing that only precursor ions 1221 and 1222 are possible, the columns of the mass filter matrix can be reduced to correspond to possible precursor ions 1221 and 1222. Precursor ions 1221 and 1222 only appear at 2 and 3 m/z in the precursor ion mass range. As a result, columns 1, 4, and 5 of mass filter matrix 871 are known to not include the solution and can be eliminated. Eliminating these columns means that their corresponding rows in precursor ion column matrix 872 can also be eliminated.

As a result, multiplication equation 870 is reduced to multiplication equation 1270. The 9×5 mass filter matrix 871 is reduced to 9×2 mass filter matrix 1271, and the 5 rows of precursor ion column matrix 872 are reduced to 2 rows in precursor ion column matrix 1272.

One of ordinary skill in the art can appreciate, that using the precursor ion scan has reduced the complexity of the problem. In addition, this means that the problem can be solved faster and with less computing resources.

Returning to FIG. 11, in various embodiments, the trace can also be optimized using isotope information obtained from the precursor ion spectrum. For example, processor 1150 determines actual or theoretical precursor ion isotopes from the precursor ion spectrum. Processor 1150 calculates a distribution of the actual or theoretical precursor ion isotopes across the precursor ion mass range of interest. Finally, processor 1150 creates the rows, n, of the mass filter matrix, the columns, m, of the mass filter matrix, the rows, m, of the unknown precursor ion column matrix, and the rows, n, of the trace column matrix according to the isotope distribution.

In various embodiments, the precursor ion spectrum is used to apply intensity constraints for each weighted coefficient, ensuring meaningful results and reducing outliers and false negatives. For example, processor 1150 determines precursor ion intensities from the precursor ion spectrum. Processor 1150 weights the elements of the mass filter matrix according to the precursor ion intensities to reduce the number of outlier and false negative results.

In various embodiments, the precursor ion spectrum is used to optimize the matrix. For example, processor 1150 determines precursor ion intensities from the precursor ion spectrum. These intensities are used as an upper bound constraint for the numerical method used to solve multiplication equation). For example, a threshold is applied to each precursor ion intensity. The threshold is then used to optimize (reduce) the columns of the mass filter matrix to those that correspond to precursors with intensity above the threshold. This makes the multiplication equation problem more stable in a numerical sense.

To control numerical optimization, (in addition to the above), processor 1150 calculates the sparsity of the trace column matrix and uses it for optimizing the solution under an assumption of Poisson noise (which is applicable since ion arrival is following Poisson process).

In various embodiments, system 1101 further includes sample introduction device 1160. Sample introduction device 1160 introduces one or more compounds of interest from a sample to ion source device 1110 at each acquisition time of a plurality of acquisition times. A scanning DIA experiment is then performed at each acquisition time of a plurality of acquisition times. As a result, a solution for the unknown precursor ion column matrix is produced for each acquisition time of a plurality of acquisition times. These solutions are combined into a precursor ion matrix, where the plurality of acquisition times are the columns of the matrix.

In various embodiments, the columns of the precursor ion matrix are combined to provide improved intensities for one or more precursor ion m/z values corresponding to the selected product ion. The columns are combined using prior knowledge across the column dimension, for example. In other words, the result has to follow an LC peak shape if it was an LC experiment, or be constant if it was infusion experiment, the most likely correct answer is found under assumptions of a result values distribution across rows and columns of precursor ion matrix.

In various embodiments, the columns of the precursor ion matrix are compared to find inconsistencies in the intensities found for one or more precursor ion m/z values corresponding to the selected product ion. In other words, the precursor ion matrix is used to flag potential errors in the one or more precursor ion m/z values found for the selected product ion.

Figure 13:
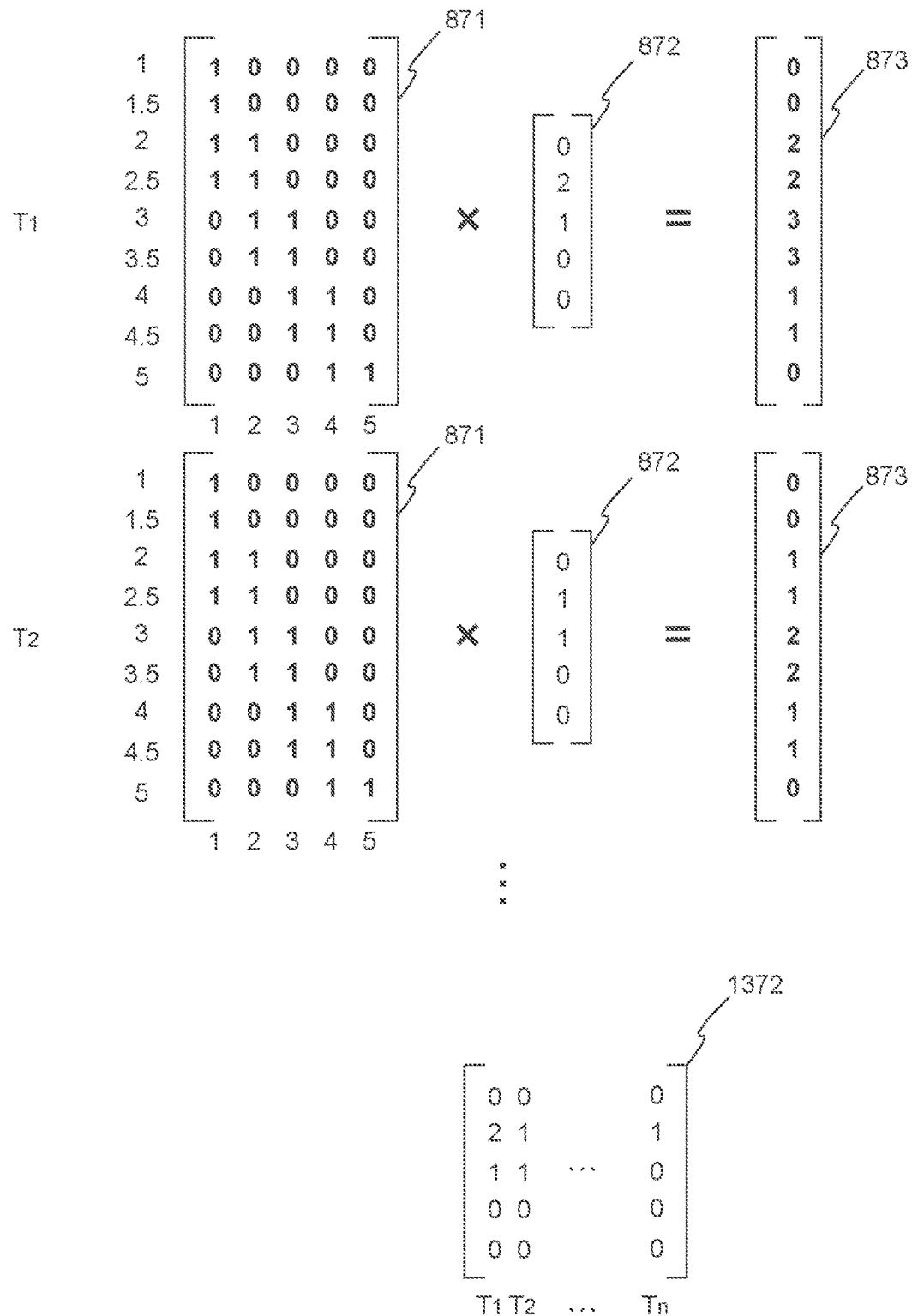
FIG. 13 is a diagram showing how the matrix multiplication equation of FIG. 8 is solved for each scanning DIA experiment performed at each acquisition time of a plurality of acquisition times as one or more compounds of interest from a sample are introduced using a sample introduction device, in accordance with various embodiments.

FIG. 13 is a diagram 1300 showing how the matrix multiplication equation of FIG. 8 is solved for each scanning DIA experiment performed at each acquisition time of a plurality of acquisition times as one or more compounds of interest from a sample are introduced using a sample introduction device, in accordance with various embodiments. In FIG. 13, at acquisition time $T_1$ a scanning DIA experiment performed. A solution for unknown precursor ion column matrix 872 is found from mass filter matrix 871 and the measured intensity values of QIT column matrix 873 at acquisition time $T_1$. At acquisition time $T_2$, another scanning DIA experiment performed. Another solution for unknown precursor ion column matrix 872 is found from mass filter matrix 871 and the measured intensity values of QIT column matrix 873 at acquisition time $T_2$. This is continued for n acquisition times, for example.

The problem then becomes multidimensional. It can be solved as a two-dimensional basis vector, or as multiple one-dimensional problems, where the results of the multiple one-dimensional problems under prior knowledge about other dimensions (monotonic, Gaussian, like in the time domain.). An exemplary two-dimensional basis vector can include, for example, the n solutions for unknown precursor ion column matrix 872 combined in precursor ion matrix 1372. The columns of precursor ion matrix 1372 represent the acquisition times $T_1, T_1, \ldots, T_n$.

Figure 14:
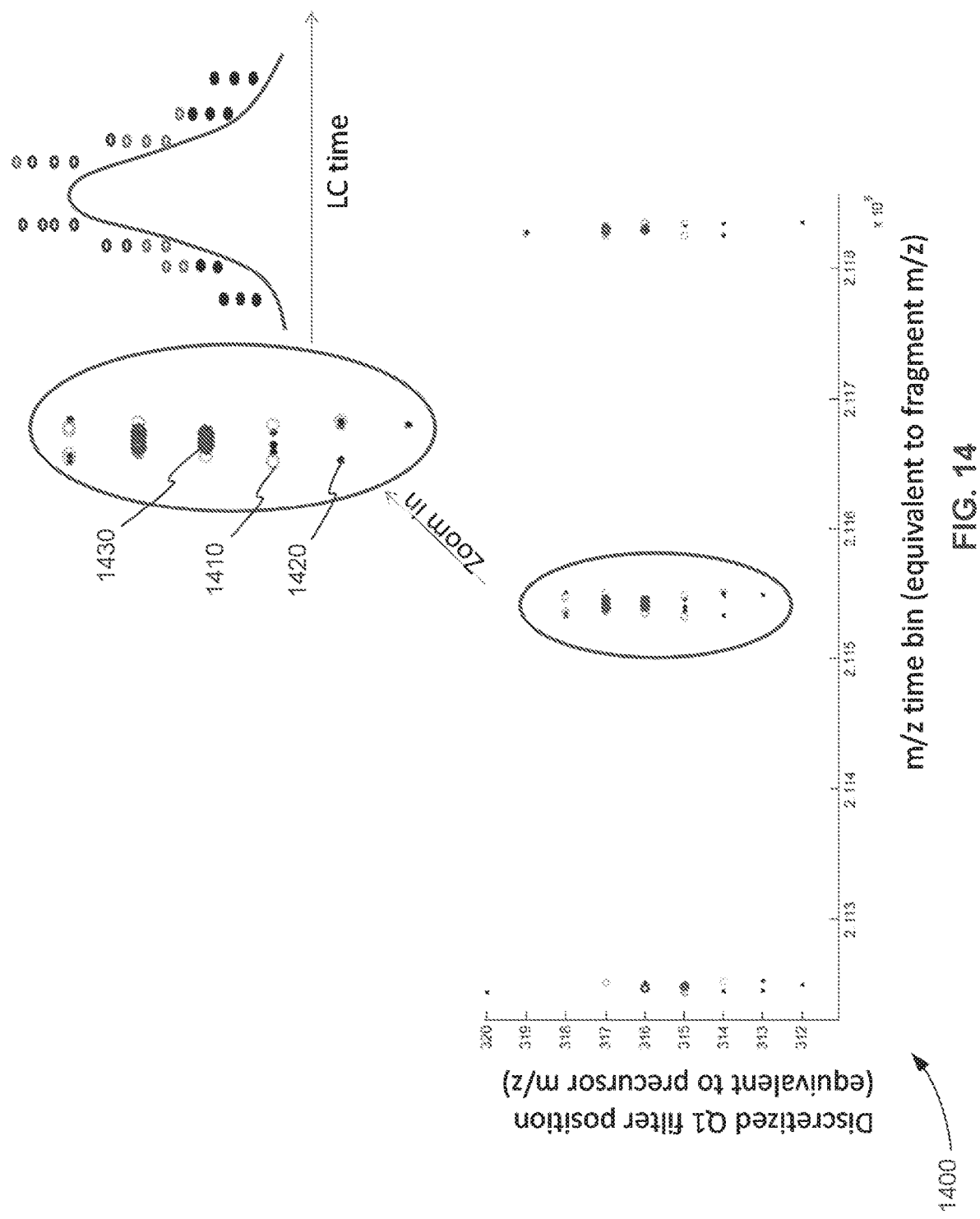
FIG. 14 is an exemplary plot showing how columns of a precursor ion matrix are combined using assumptions about a result values distribution across rows and columns of precursor ion matrix, in accordance with various embodiments.

FIG. 14 is an exemplary plot 1400 showing how columns of a precursor ion matrix are combined using assumptions about a result values distribution across rows and columns of precursor ion matrix, in accordance with various embodiments. Marker 1410 represents inferred precursor ion m/z values using a first method. Marker 1420 represents inferred precursor ion m/z values using a second method. Marker 1430 represents the most confident inference value in either method. Each of markers 1410, 1420, and 1430 are obtained at one LC cycle, for example. Confidence is a measure of the uncertainty of the result and is calculated accordingly to each method used. The distribution of uncertainty measure is shown in plot 1400.

Method for Identifying a Precursor Ion from a Product Ion

Figure 15:
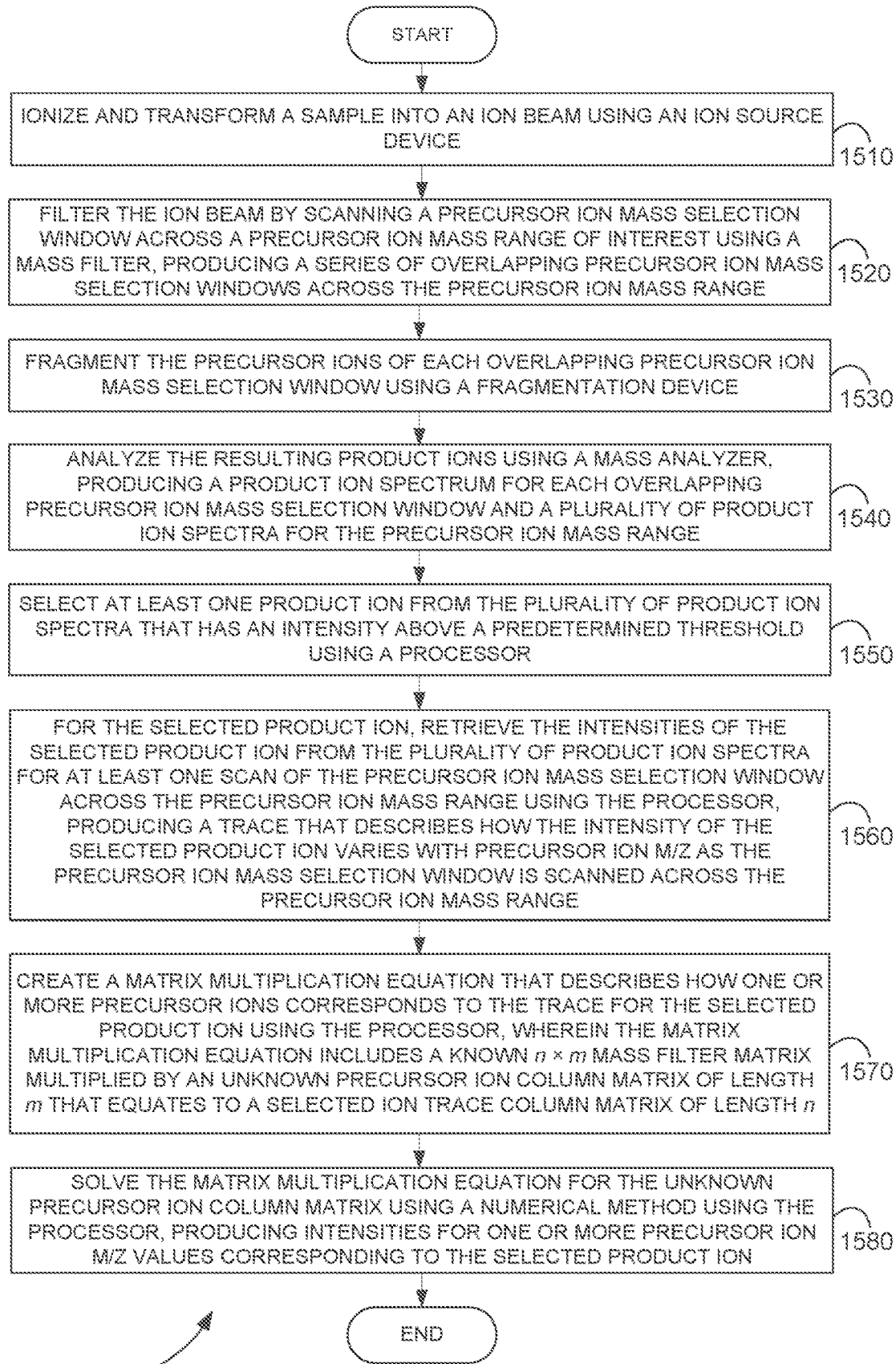
FIG. 15 is a flowchart showing a method for identifying a precursor ion of a product ion in a scanning DIA tandem mass spectrometry experiment, in accordance with various embodiments.

FIG. 15 is a flowchart 1500 showing a method for identifying a precursor ion of a product ion in a scanning DIA tandem mass spectrometry experiment, in accordance with various embodiments.

In step 1510 of method 1500, a sample is ionized and transformed into an ion beam using an ion source device.

In step 1520, the ion beam is filtered by scanning a precursor ion mass selection window across a precursor ion mass range of interest using a mass filter. A series of overlapping precursor ion mass selection windows are produced across the precursor ion mass range.

In step 1530, the precursor ions of each overlapping precursor ion mass selection window are fragmented using a fragmentation device.

In step 1540, the resulting product ions are analyzed using a mass analyzer. A product ion spectrum is produced for each overlapping precursor ion mass selection window resulting in a plurality of product ion spectra for the precursor ion mass range.

In step 1550, at least one product ion is selected from the plurality of product ion spectra that has an intensity above a predetermined threshold using a processor.

In step 1560, for the selected product ion, the intensities of the selected product ion are retrieved from the plurality of product ion spectra for at least one scan of the precursor ion mass selection window across the precursor ion mass range using the processor. A trace is produced that describes how the intensity of the selected product ion varies with precursor ion m/z as the precursor ion mass selection window is scanned across the precursor ion mass range.

In step 1570, a matrix multiplication equation is created that describes how one or more precursor ions corresponds to the trace for the selected product ion using the processor. The matrix multiplication equation includes a known n×m mass filter matrix multiplied by an unknown precursor ion column matrix of length m that equates to a selected ion trace column matrix of length n.

In step 1580, the matrix multiplication equation is solved for the unknown precursor ion column matrix using a numerical method using the processor. Intensities for one or more precursor ion m/z values are produced corresponding to the selected product ion.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying a precursor ion of a product ion in a scanning data-independent acquisition (DIA) tandem mass spectrometry experiment, comprising:
   a. an ion source device that transforms a sample into an ion beam;
   b. a mass filter that receives the ion beam and filters the ion beam by scanning a precursor ion mass selection window across a precursor ion mass range of interest, producing a series of overlapping precursor ion mass selection windows across the precursor ion mass range;
   c. a fragmentation device that receives the precursor ions of each overlapping precursor ion mass selection window and fragments the precursor ions of each overlapping precursor ion mass selection window;
   d. a mass analyzer that receives the product ions from each fragmentation of each overlapping precursor ion mass selection window and analyzes the resulting product ions, producing a product ion spectrum for each overlapping precursor ion mass selection window and a plurality of product ion spectra for the precursor ion mass range; and
   e. a processor in communication with the mass filter and the mass analyzer that
      receives the plurality of product ion spectra produced by the series of overlapping precursor ion mass selection windows,
      selects at least one product ion from the plurality of product ion spectra that has an intensity above a predetermined threshold,
      for the selected product ion, retrieves the intensities of the selected product ion from the plurality of product ion spectra for at least one scan of the precursor ion mass selection window across the precursor ion mass range, producing a trace that describes how the intensity of the selected product ion varies with precursor ion mass-to-charge ratio (m/z) as the precursor ion mass selection window is scanned across the precursor ion mass range,
      creates a matrix multiplication equation that describes how the one or more precursor ions corresponds to the trace for the selected product ion, wherein the matrix multiplication equation includes a known n×m mass filter matrix multiplied by an unknown precursor ion column matrix of length m that equates to a selected ion trace column matrix of length n, and
      solves the matrix multiplication equation for the unknown precursor ion column matrix using a numerical method, producing intensities for one or more precursor ion m/z values corresponding to the selected product ion.

2. The system of claim 1, wherein the numerical method comprises non-negative least squares (NNLS).

3. The system of claim 1,
   wherein rows, n, of the mass filter matrix are the locations of the precursor ion mass selection window across the precursor ion mass range, the columns, m, of the mass filter matrix are the precursor ion m/z values across the precursor ion mass range, and the elements of the mass filter matrix represent the transmission or non-transmission by the precursor ion mass selection window,
   wherein rows, m, of the unknown precursor ion column matrix correspond to the columns of the mass filter matrix and are the precursor ion m/z values across the precursor ion mass range, and the elements of the unknown precursor ion column matrix are the intensities of the precursor ions corresponding to the selected product ion,
   wherein the rows, n, of the trace column matrix correspond to the rows of the mass filter matrix and are the locations of the precursor ion mass selection window across the precursor ion mass range, and the elements of the trace column matrix are the intensities of the selected product ion at locations of the precursor ion mass selection window across the precursor ion mass range.

4. The system of claim 3,
   wherein the mass filter, before filtering the ion beam by scanning a precursor ion mass selection window across a precursor ion mass range of interest, filters the ion beam for precursor ions in the precursor ion mass range of interest, producing a plurality of precursor ions, and
   wherein the mass analyzer analyzes the plurality of precursor ions, producing a precursor ion spectrum.

5. The system of claim 4, wherein the processor further, for each precursor ion m/z value with an intensity above a precursor ion intensity threshold in the precursor ion spectrum, creates a possible precursor ion m/z value, producing a plurality of possible precursor ion m/z values across the precursor ion mass range.

6. The system of claim 5, wherein the processor reduces columns, m, of the n×m mass filter matrix, and the columns of the unknown precursor ion column matrix to correspond to the plurality of possible precursor ion m/z values.

7. The system of claim 4, wherein the processor determines actual or theoretical precursor ion isotopes from the precursor ion spectrum, calculates a distribution of the actual or theoretical precursor ion isotopes across the precursor ion mass range of interest, and creates the rows, n, of the mass filter matrix, the columns, m, of the mass filter matrix, and the rows, m, of the unknown precursor ion column matrix according to the isotope distribution.

8. The system of claim 4, the processor determines precursor ion intensities from the precursor ion spectrum and weights the elements of the mass filter matrix according to the precursor ion intensities to reduce the number of outlier and false negative results.

9. The system of claim 4, wherein the processor determines precursor ion intensities from the precursor ion spectrum and uses the precursor ion intensities as an upper bound for the values of precursor ion column matrix in the solution of the matrix multiplication equation.

10. The system of claim 1, further comprising
    a sample introduction device that introduces one or more compounds of interest from a sample to ion source device at each acquisition time of a plurality of acquisition times, wherein steps a-e are performed at each acquisition time of a plurality of acquisition times, producing a solution for the unknown precursor ion column matrix for each acquisition time of a plurality of acquisition times.

11. The system of claim 10, wherein the processor further combines the solutions for the unknown precursor ion column matrix for each acquisition time of a plurality of acquisition times into a precursor ion matrix, wherein the plurality of acquisition times are the columns of the precursor ion matrix.

12. The system of claim 11, wherein the processor further combines the columns of the precursor ion matrix to provide improved intensities for one or more precursor ion m/z values corresponding to the selected product ion.

13. A method for identifying a precursor ion of a product ion in a scanning data-independent acquisition (DIA) tandem mass spectrometry experiment, comprising:
- ionizing and transforming a sample into an ion beam using an ion source device;
- filtering the ion beam by scanning a precursor ion mass selection window across a precursor ion mass range of interest using a mass filter, producing a series of overlapping precursor ion mass selection windows across the precursor ion mass range;
- fragmenting the precursor ions of each overlapping precursor ion mass selection window using a fragmentation device;
- analyzing the resulting product ions using a mass analyzer, producing a product ion spectrum for each overlapping precursor ion mass selection window and a plurality of product ion spectra for the precursor ion mass range;
- selecting at least one product ion from the plurality of product ion spectra that has an intensity above a predetermined threshold using a processor;
- for the selected product ion, retrieving the intensities of the selected product ion from the plurality of product ion spectra for at least one scan of the precursor ion mass selection window across the precursor ion mass range using the processor, producing a trace that describes how the intensity of the selected product ion varies with precursor ion mass-to-charge ratio (m/z) as the precursor ion mass selection window is scanned across the precursor ion mass range;
- creating a matrix multiplication equation that describes how one or more precursor ions corresponds to the trace for the selected product ion using the processor, wherein the matrix multiplication equation includes a known n×m mass filter matrix multiplied by an unknown precursor ion column matrix of length m that equates to a selected ion trace column matrix of length n; and
- solving the matrix multiplication equation for the unknown precursor ion column matrix using a numerical method using the processor, producing intensities for one or more precursor ion m/z values corresponding to the selected product ion.

14. The method of claim 13, wherein the numerical method comprises non-negative least squares (NNLS).

15. The method of claim 13, wherein
- wherein rows, n, of the mass filter matrix are the locations of the precursor ion mass selection window across the precursor ion mass range, the columns, m, of the mass filter matrix are the precursor ion m/z values across the precursor ion mass range, and the elements of the mass filter matrix represent the transmission or non-transmission by the precursor ion mass selection window,
- wherein rows, m, of the unknown precursor ion column matrix correspond to the columns of the mass filter matrix and are the precursor ion m/z values across the precursor ion mass range, and the elements of the unknown precursor ion column matrix are the intensities of the precursor ions corresponding to the selected product ion,
- wherein the rows, n, of the trace column matrix correspond to the rows of the mass filter matrix and are the locations of the precursor ion mass selection window across the precursor ion mass range, and the elements of the trace column matrix are the intensities of the selected product ion at locations of the precursor ion mass selection window across the precursor ion mass range.

* * * * *